US012779248B2

(12) United States Patent
Fu et al.

(10) Patent No.: US 12,779,248 B2
(45) Date of Patent: Nov. 3, 2026

(54) RADIOTHERAPY SYSTEMS AND METHODS

(71) Applicant: SHANGHAI UNITED IMAGING HEALTHCARE CO., LTD., Shanghai (CN)

(72) Inventors: Feichao Fu, Shanghai (CN); Cheng Ni, Shanghai (CN); Jun Bao, Shanghai (CN); Qiang Zhang, Shanghai (CN); Chao Wang, Shanghai (CN); Wei Zhang, Shanghai (CN); Shitao Liu, Shanghai (CN); Li Wang, Shanghai (CN); Tuoyu Cao, Shanghai (CN); Can Liao, Shanghai (CN); Tuota Xing, Shanghai (CN); Wei Qi, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 216 days.

(21) Appl. No.: 18/665,637

(22) Filed: May 16, 2024

(65) Prior Publication Data

US 2024/0299774 A1 Sep. 12, 2024

Related U.S. Application Data

(63) Continuation of application No. PCT/CN2021/138073, filed on Dec. 14, 2021.

(51) Int. Cl.
*A61N 5/10* (2006.01)

(52) U.S. Cl.
CPC ......... *A61N 5/1049* (2013.01); *A61N 5/1081* (2013.01); *A61N 2005/1052* (2013.01); *A61N 2005/1055* (2013.01)

(58) Field of Classification Search
CPC ................ A61N 5/1049; A61N 5/1081; A61N 2005/1052; A61N 2005/1055;
(Continued)

(56) References Cited

U.S. PATENT DOCUMENTS

| | | | |
|---|---|---|---|
| 11,090,012 | B2 | 8/2021 | Fang et al. |
| 2008/0139924 | A1 | 6/2008 | Eberler et al. |

(Continued)

FOREIGN PATENT DOCUMENTS

| | | | |
|---|---|---|---|
| CN | 104161532 A | 11/2014 | |
| CN | 104146725 B | 8/2016 | |

(Continued)

OTHER PUBLICATIONS

International Search Report in PCT/CN2021/138073 mailed on Sep. 14, 2022, 8 pages.

(Continued)

*Primary Examiner* — Courtney D Thomas
(74) *Attorney, Agent, or Firm* — METIS IP LLC

(57) ABSTRACT

Embodiments of the present disclosure provide a radiotherapy system, comprising a first imaging component, a second imaging component, and a treatment component. The first imaging component and second imaging component may be used to determine a target region of an object and/or to guide an emission of treatment rays. The treatment component may be used to emit the treatment rays toward the target region. An isocenter of the treatment component may coincide with an isocenter of the second imaging component.

20 Claims, 14 Drawing Sheets

200

(58) Field of Classification Search
CPC .. A61N 2005/1061; A61N 5/10; A61B 5/055; A61B 6/00
See application file for complete search history.

(56) References Cited

U.S. PATENT DOCUMENTS

| | | | | |
|---|---|---|---|---|
| 2012/0150017 | A1* | 6/2012 | Yamaya | G01R 33/481 600/411 |
| 2012/0253174 | A1 | 10/2012 | Popescu | |
| 2013/0225975 | A1 | 8/2013 | Harvey | |
| 2014/0135615 | A1* | 5/2014 | Kruip | A61N 5/1081 600/411 |
| 2015/0209600 | A1 | 7/2015 | Overweg | |
| 2016/0256713 | A1 | 9/2016 | Saunders et al. | |
| 2019/0184197 | A1 | 6/2019 | Fallone et al. | |
| 2020/0246637 | A1 | 8/2020 | Wang et al. | |
| 2021/0162236 | A1 | 6/2021 | Shvartsman et al. | |

FOREIGN PATENT DOCUMENTS

| | | | |
|---|---|---|---|
| CN | 109646031 | A | 4/2019 |
| CN | 209847209 | U | 12/2019 |
| CN | 108295386 | B | 6/2020 |

OTHER PUBLICATIONS

Written Opinion in PCT/CN2021/138073 mailed on Sep. 14, 2022, 8 pages.

* cited by examiner

200

Replacement Sheet 3/6

RADIOTHERAPY SYSTEMS AND METHODS

CROSS REFERENCE TO RELATED APPLICATIONS

This application is a continuation of International Patent Application No. PCT/CN2021/138073, filed on Dec. 14, 2021, the entire contents of which are incorporated herein by reference.

TECHNICAL FIELD

The present disclosure relates to the technical field of medical devices, and in particular, to radiotherapy systems and methods.

BACKGROUND

Radiotherapy is the method of performing a localized treatment on a specific target region (e.g., a malignant tumor) using radiation. While preparing or implementing the radiotherapy, the location, shape, size, etc. of the target region may change. As a result, imaging may be required to assist in monitoring the target region to determine or adjust a treatment plan. Positron Emission Tomography (PET) and Magnetic Resonance Imaging (MRI) can both be used to determine or monitor the target region, but PET and MRI have different advantages and disadvantages. Therefore, there is a need to provide an improved radiotherapy system that fully integrates functions of PET and MRI, henceforth improving the effectiveness of imaging guidance and treatment.

SUMMARY

One of the embodiments of the present disclosure provides a radiotherapy system. The radiotherapy system may comprise a first imaging component and a second imaging component, and a treatment component. The first imaging component and the second imaging component may be configured to determine a target region of an object and/or guide an emission of treatment rays. The treatment component may be configured to emit the treatment rays toward the target region. An isocenter of the treatment component may coincide with an isocenter of the second imaging component.

In some embodiments, the treatment component comprises a gantry and a radiation source disposed within the gantry.

In some embodiments, the first imaging component is disposed at an end of the second imaging component along an axial direction of the second imaging component.

In some embodiments, the second imaging component comprises a main magnet and a gradient coil. The gradient coil is disposed on an inner side of the main magnet along a radial direction of the main magnet, an hollow space is formed on a side of the gradient coil along an axial direction of the gradient coil, and the first imaging component is located within the hollow space.

In some embodiments, the first imaging component at least partially protrudes out of the hollow space along an axial direction of the first imaging component.

In some embodiments, the second imaging component comprises a gradient coil and a radio frequency coil, and the first imaging component is disposed between the gradient coil and the radio frequency coil.

In some embodiments, the first imaging component is disposed on an inner side of the second imaging component along a radial direction of the second imaging component.

In some embodiments, an isocenter of the first imaging component coincides with the isocenter of the second imaging component.

In some embodiments, the first imaging component is disposed adjacent to the second imaging component along an axial direction.

In some embodiments, the treatment component is rotatable and the first imaging component and the second imaging component are stationary.

In some embodiments, the second imaging component includes a first portion and a second portion, and at least one of the treatment component or the first imaging component are disposed between the first portion and the second portion.

In some embodiments, the first imaging component includes two portions disposed opposite to each other with respect to a radiation source of the treatment component.

In some embodiments, the two portions of the first imaging component are movable.

In some embodiments, the first imaging component rotates in synchronization with the treatment component.

In some embodiments, an isocenter of the first imaging component coincides with the isocenter of the second imaging component.

In some embodiments, the treatment component is disposed on the second imaging component, the first imaging component is disposed within the second imaging component, and the second imaging component is rotatable.

In some embodiments, the first imaging component is a positron emission computed tomography (PET) device, the treatment component is a linear accelerator (Linac), and the second imaging component is a magnetic resonance imaging (MRI) device.

One of the embodiments of the present disclosure provides a radiotherapy method. The method may comprise determining a first image and/or a second image including a target region of an object via a first imaging component and/or a second imaging component. The method may further comprise guiding a treatment component to emit treatment rays toward the target region based on the first image and/or the second image, wherein an isocenter of the treatment component coincides with an isocenter of the second imaging component.

BRIEF DESCRIPTION OF THE DRAWINGS

The present disclosure will be further illustrated by way of exemplary embodiments, which will be described in detail by means of the accompanying drawings. These embodiments are not limiting, and in these embodiments, the same numbering denotes the same structure, wherein.

DETAILED DESCRIPTION

In order to more clearly illustrate the technical solutions of the embodiments of the present disclosure, the following will briefly describe the accompanying drawings that need to be used in the description of the embodiments. Obviously, the accompanying drawings in the following description are only some examples or embodiments of the present disclosure, and it is possible for a person of ordinary skill in the art to apply the present disclosure to other similar scenarios in accordance with these drawings without creative labor.

It should be understood that the terms "system", "device" as used herein, "unit" and/or "module" as used herein is a way to distinguish between different components, elements, parts, sections, or assemblies at different levels. However, the words may be replaced by other expressions if other words accomplish the same purpose.

As shown in the present disclosure and claims herein, unless the context clearly suggests an exception, the words "one," "a," "an," "a kind," and/or "the" do not refer specifically to the singular, but may also include the plural. Generally, the terms "including" and "comprising" suggest only the inclusion of clearly identified steps and elements, yet the steps and elements do not constitute an exclusive list, and the method or apparatus may also include other steps or elements.

Flowcharts are used in the present disclosure to illustrate operations performed by a system according to embodiments of the present disclosure. It should be appreciated that the preceding or following operations are not necessarily performed in an exact sequence. Instead, steps may be processed in reverse order or simultaneously. Also, it is possible to add other operations to these processes, or to remove a step or steps from these processes.

Figure 1:
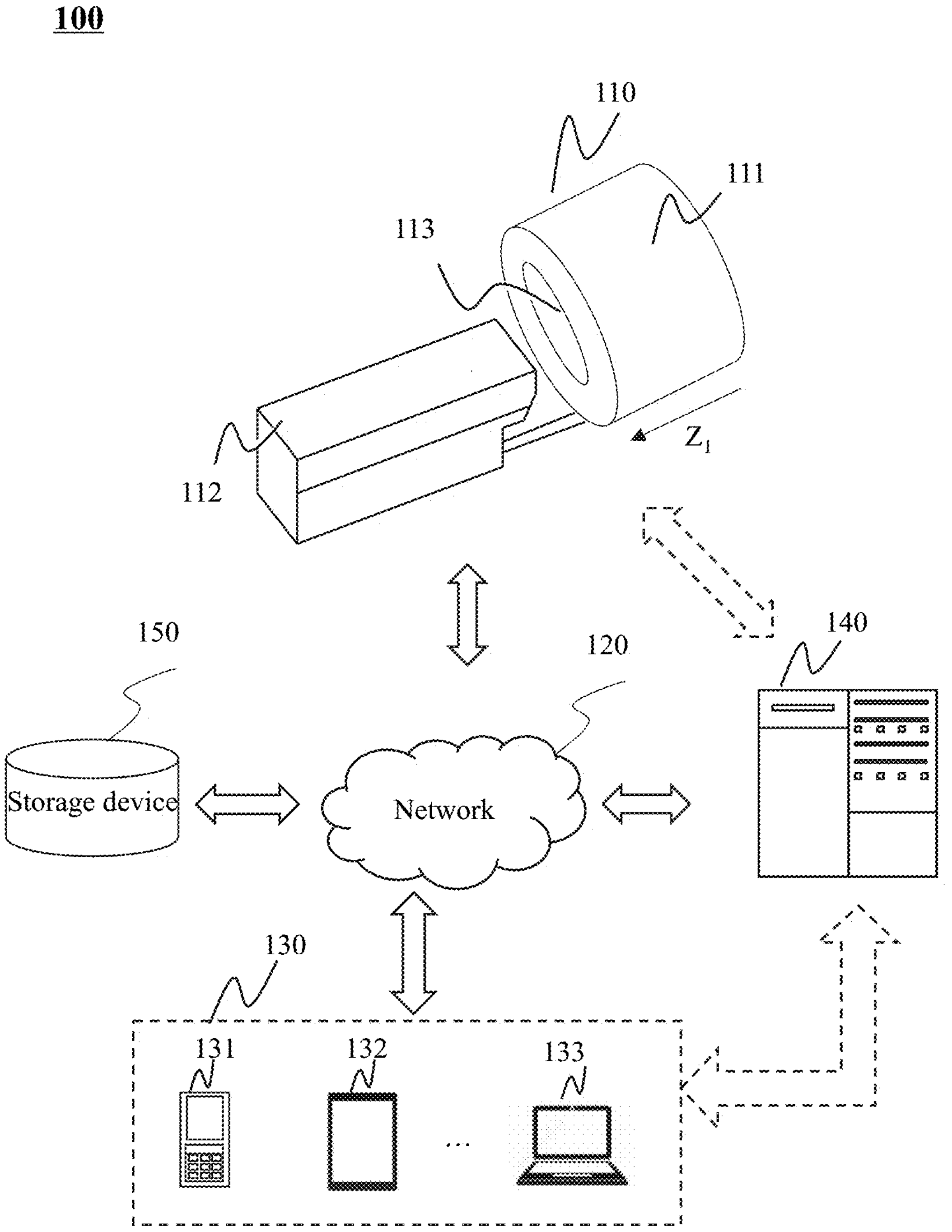
FIG. 1 is a schematic diagram illustrating an exemplary application scenario of a radiotherapy system according to some embodiments of the present disclosure.

FIG. 1 is a schematic diagram illustrating an exemplary application scenario of a radiotherapy system according to some embodiments of the present disclosure. In some embodiments, as shown in FIG. 1, a radiotherapy system 100 may include a medical device 110, a network 120, a terminal device 130, a processing device 140, and a storage device 150. Components of the radiotherapy system 100 may be interconnected with each other via the network 120. For example, the medical device 110 and the terminal device 130 may be connected or in communication via the network 120. In some embodiments, the radiotherapy system 100 may provide radiotherapy to a lesion (e.g., a tumor) of a patient, and the radiotherapy may include a stereotactic radiosurgery, a precision radiation therapy, etc.

The medical device 110 may include a medical assembly 111, a bed 112, and a bore 113. In some embodiments, the medical assembly 111 may have a hollow cannular structure (e.g., a hollow cylinder). An inner annular surface of the cannular structure may form the bore 113, and the medical assembly 111 may perform an imaging or a treatment on an object located in the bore 113. The bed 112 may be configured to support the object. In some embodiments, the bed 112 may be movable along a plurality of directions to facilitate moving the object to a suitable location for imaging or treatment. For example, the bed 112 may move along an axial direction (e.g., a $Z_1$ direction shown in FIG. 1) of the medical assembly 111 to move the object into a radiation field of the medical device 110.

In some embodiments, the medical assembly 111 may include a treatment component, a first imaging component, and a second imaging component. In some embodiments, the treatment component may be configured to emit treatment rays to a target region of the object to perform a radiotherapy on the target region. In some embodiments, the first imaging component and/or the second imaging component may be configured to determine the target region of the object and/or guide an emission of the treatment rays.

In some embodiments, the first imaging component and/or the second imaging component may obtain an image associated with the target region before the radiotherapy is performed on the target region. The radiotherapy system 100 or a user (e.g., a clinician) may develop a treatment plan (e.g., outlining a target area, determining a radiation dose, etc.) for the target region based on the obtained image. In some embodiments, the first imaging component and/or the second imaging component may guide the emission of the treatment rays during the radiotherapy of the target region. For example, the first imaging component and/or the second imaging component may guide the emission of the treatment rays by tracking the target region in real-time, resetting the target region between treatment fractions, or the like. In some embodiments, after the radiotherapy of the target region, the first imaging component and/or the second imaging component may obtain an image of the target region and/or an image of a normal tissue surrounding the target region. The radiotherapy system 100 or the user (e.g., a clinician) may evaluate a result of the radiotherapy of the target region based on the obtained image (e.g., how boundaries of the target region have changed, a bio metabolic profile of the target region, etc.).

In some embodiments, the treatment component may include a radiotherapy device such as a Linear Electron Accelerator (Linac), an X-ray therapy device, or the like. The first imaging component and/or the second imaging component may include a positron emission computed tomography (PET) device, a magnetic resonance imaging (MRI) device, an electron computed tomography (CT) device, or the like. For convenience of description, the following descriptions provide exemplary embodiments in which the treatment component is a Linac, the first imaging component is a PET, and the second imaging component is an MRI. It is understood that a structure of the Linac typically includes a gantry, a radiation source disposed on the gantry, and other components, etc., and a structure of the PET typically includes a gantry, a detector disposed on the gantry, and other components, etc. For convenience of description, in the present disclosure, the treatment component may refer to a treatment component as a whole or a radiation source thereof, and the first imaging component may refer to an imaging component thereof or a detector thereof.

In some embodiments, the treatment component may include a gantry and a radiation source disposed on the gantry. In some embodiments, the radiation source may be disposed inside or outside the gantry. In some embodiments, the gantry may be an annular gantry, and the radiation source may be disposed inside the annular gantry. In some embodiments, the gantry may rotate around an object (e.g., a patient) that is moved into a radiation field of the treatment component to facilitate the emission of treatment rays by the radiation source to a target region of the object. In some embodiments, the gantry may rotate along a first axis. In some embodiments, the gantry may utilize a winding frame structure, a slip ring structure, etc., or any combination thereof. In some embodiments, the radiation source may be disposed within the second imaging component. In some embodiments, the treatment component may include a detector disposed on the gantry. The detector may be used to receive at least a portion of the treatment rays emitted by the radiation source. In some embodiments, the second imaging component may be a hollow annular structure, and the hollow annular structure has a second axis. In some embodiments, the second axis may coincide with the first axis.

In some embodiments, an isocenter of the treatment component may coincide with an isocenter of the second imaging component. In some embodiments, the isocenter of the treatment component coincides with an isocenter of the second imaging component may refer to a deviation between the isocenter of the treatment component and the isocenter of the second imaging component is within a preset range (e.g., 1 mm, 2 mm, etc.). In such cases, a therapeutic region of the treatment component may at least partially overlap with an imaging region of the second imaging component. In some embodiments, the target region of the object (e.g., a region to be treated) may be imaged and treated by placing the target region of the object in this overlapping region. Because the target region is located within the overlapping region, there is no need to move the bed or the patient during the imaging and treatment. In this way, errors in imaging data due to moving the bed or the patient can be avoided, thus avoiding a deviation of the treated region in the radiotherapy from a region planned to be treated in the radiotherapy, thus ensuring the effect of the radiotherapy. In addition, since there is no need to move the bed or the patient or perform subsequent repositioning, a radiotherapy time can be shortened, thus alleviating the pain of the patient. Furthermore, since the target region is located in the overlapping region, the second imaging component may track a treatment process in real-time during the radiotherapy so as to provide timely feedback on changes in the target region. If necessary, the treatment component may adjust the treatment plan or interrupt the radiotherapy, thereby effectively improving the accuracy and efficiency of the radiotherapy, and minimizing damage to the patient's healthy tissues while ensuring that sufficient radiation dose is delivered to the target region.

In some embodiments, the first imaging component may be disposed at the end of the second imaging component along an axial direction of the second imaging component. The axial direction of the second imaging component refers to a direction parallel to the second axis of the second imaging component (e.g., the $Z_1$ direction shown in FIG. 1).

In some embodiments, the second imaging component may include a main magnet and a gradient coil. The gradient coil may be disposed on an inner side of the main magnet along a radial direction of the main magnet, and an axial length of the gradient coil is smaller than an axial length of the main magnet. In some embodiments, a side of the gradient coil along the axial direction may form a hollow space. The first imaging component may be located within the hollow space. In some embodiments, the first imaging component may at least partially protrude out of the hollow space along an axial direction of the first imaging component. In such embodiments, the first imaging component may fully utilize the hollow space within the second imaging component, resulting in a more compact overall structure, thereby saving space.

In some embodiments, the first imaging component may be disposed between the main magnet and the gradient coil of the second imaging component. In some embodiments, the first imaging component may be disposed between the gradient coil and a radio frequency coil of the second imaging component.

In some embodiments, the first imaging component may be disposed on an inner side of the second imaging component along a radial direction of the second imaging component. The radial direction of the second imaging component refers to a direction in which a diameter of an annular cross-section of the second imaging component lies.

In some embodiments, an isocenter of the first imaging component may coincide with the isocenter of the second imaging component. In some embodiments, an isocenter of the treatment component may coincide with the isocenter of the first imaging component and the isocenter of the second imaging component. In some embodiments, the an isocenter of the treatment component coincides with the isocenter of the first imaging component and the isocenter of the second imaging component may refer to a deviation between any two of the isocenters of the treatment component, the first imaging component, and the second imaging component is within a preset range (e.g., 1 mm, 2 mm, etc.). In such a case, the therapeutic region of the treatment component, the imaging region of the first imaging component may at least partially overlap with the imaging region of the second imaging component. In some embodiments, the treatment component may place the target region of the object in this overlapping region for imaging and treatment. Because the target region is located within the overlapping region, there is no need to move the bed or the patient during the imaging and treatment. In addition, the first imaging component and the second imaging component may perform imaging jointly, which may achieve more accurate positioning, more accurate treatment plan formulation or adjustment, and more accurate real-time tracking and guiding of the treatment, thus effectively improving the accuracy of the radiotherapy.

In some embodiments, the first imaging component may be disposed adjacent to the second imaging component along the axial direction. The first imaging component is deemed as being adjacent to the second imaging component along the axial direction when there is no other component between the first imaging component and the second imaging component along the axial direction.

In some embodiments, the treatment component is rotatable, and the first imaging component and the second imaging component are stationary.

In some embodiments, the second imaging component may include a first portion and a second portion. In some embodiments, at least one of the treatment component or the first imaging component may be disposed between the first portion and the second portion of the second imaging component.

In some embodiments, the first imaging component may have a hollow cannular structure. In some embodiments, the first imaging component may be disposed on an inner annular surface of an annular gantry of the treatment component. In some embodiments, the first imaging component may be disposed on a separate annular support cylinder, the annular support cylinder may be disposed on the inner annular surface of the annular gantry of the treatment component.

In some embodiments, the first imaging component may comprise two or more portions that are disposed opposite to each other with respect to the treatment component so that the treatment rays emitted by the radiation source do not irradiate the second imaging component, thereby reducing the impact of the rays emitted by the radiation source of the treatment component on the second imaging component.

In some embodiments, the two or more portions of the first imaging component may be movable so that a region to be imaged of the object may be located in a center of an imaging region of the first imaging component, thereby improving the quality of the imaging.

In some embodiments, the second imaging component may be rotated in synchronization with the radiation source to maintain a constant relative position of the second imaging component to the radiation source.

In some embodiments, the medical assembly 111 may include at least one slip ring for supporting the first imaging component and enabling the first imaging component to move along the slip ring. In some embodiments, the medical assembly 111 may include two slip rings that are disposed symmetrically to each other with respect to the treatment component for supporting the first imaging component to make the first imaging component more stable.

In some embodiments, the isocenter of the first imaging component may coincide with the isocenter of the second imaging component.

In some embodiments, in order to protect one or more members of the treatment component (e.g., the radiation source) and one or more members of the first imaging component (e.g., the detector) from a magnetic field of the second imaging component, the medical assembly 111 may include a magnetic shielding component for shielding the magnetic field of the second imaging component. For example, the treatment component may include a magnetic shielding cover made of high magnetization and permeability, and the radiation source of the treatment component, and the detector of the first imaging component may be located within the magnetic shielding cover.

More descriptions of the medical assembly 111 can be found elsewhere in the present disclosure (e.g., FIGS. 2A-7D, and related descriptions).

The network 120 may include any suitable network capable of facilitating an exchange of information and/or data for the radiotherapy system 100. In some embodiments, at least one component of the radiotherapy system 100 may exchange information and/or data with at least one other component of the radiotherapy system 100 via the network 120. The at least one component may include the medical device 110, the terminal device 130, the processing device 140, and the storage device 150. For example, the processing device 140 may obtain an image of the object from the medical device 110 via the network 120.

The terminal device 130 may be in communication and/or connection with the medical device 110, the processing device 140, and/or the storage device 150. For example, an operator may adjust current parameters of the medical device 110 via the terminal device 130. As another example, the operator may input a scan protocol via the terminal device 130 and the processing device 140 may store the scan protocol in the storage device 150. As another example, the parameters of the medical device 110 determined by the processing device 140 may be displayed on the terminal device 130.

The processing device 140 may process data and/or information obtained from the medical device 110, the terminal device 130, the storage device 150, or other components of the radiotherapy system 100. For example, the processing device 140 may determine, via the first imaging component and the second imaging component, a first image and a second image including the target region of the object. The processing device 140 may also direct the treatment component to emit the treatment rays toward the target region based on the first image and the second image.

The storage device 150 may store data, instructions, and/or any other information. In some embodiments, the storage device 150 may store data obtained from the medical device 110, the terminal device 130, and/or the processing device 140. In some embodiments, the storage device 150 may store data and/or instructions used by the processing device 140 to execute or use to accomplish exemplary methods described in the present disclosure.

In some embodiments, the storage device 150 may be coupled to the network 120 to communicate with at least one other component of the radiotherapy system 100. The at least one component may include the medical device 110, the terminal device 130, and the processing device 140. The at least one component of the radiotherapy system 100 may access data stored in the storage device 150 via the network 120. In some embodiments, the storage device 150 may be part of the processing device 140.

It should be noted that the foregoing description is provided for illustrative purposes only and is not intended to limit the scope of the present disclosure. For a person of ordinary skill in the art, a wide variety of variations and modifications may be made under the guidance of the contents of the present disclosure. Features, structures, methods, and other characteristics of the exemplary embodiments described herein may be combined in various ways to obtain additional and/or alternative exemplary embodiments.

Figure 2A:
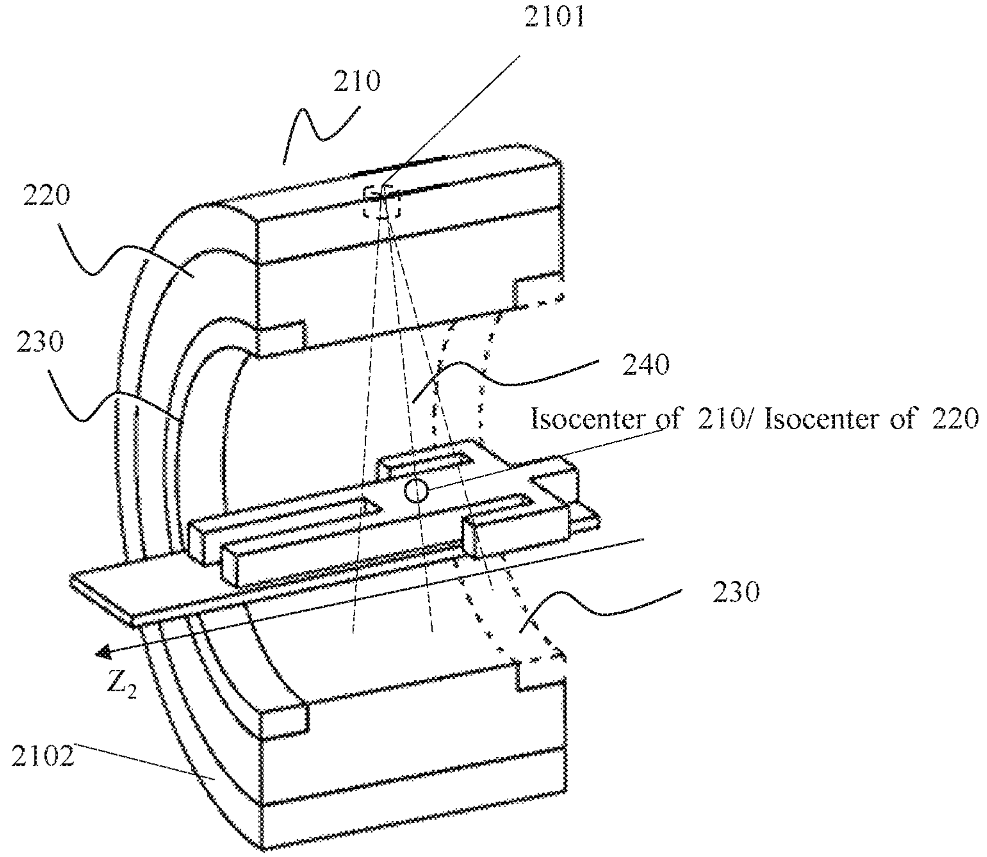
FIG. 2A is a schematic diagram illustrating an exemplary medical assembly according to some embodiments of the present disclosure.
Figure 2B:
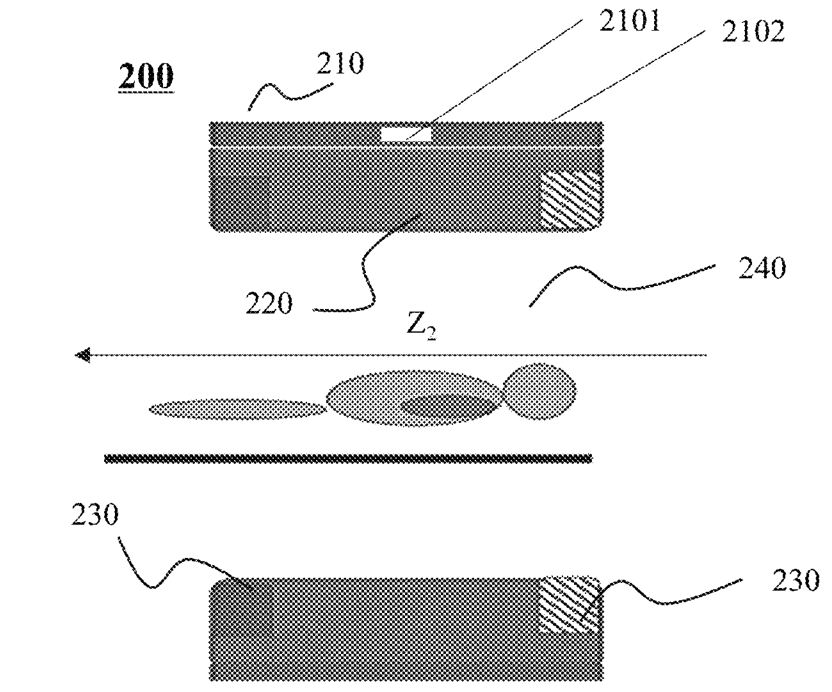
FIG. 2B is a schematic diagram illustrating an exemplary axial cross-section of a medical assembly according to some embodiments of the present disclosure.
Figure 2C:
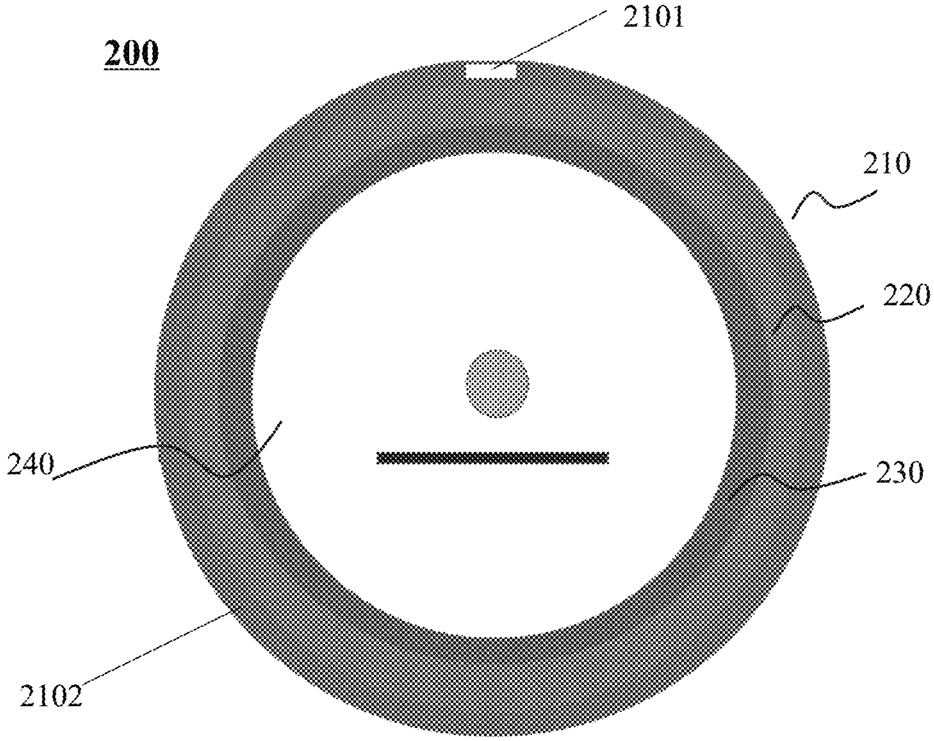
FIG. 2C is a schematic diagram illustrating an exemplary radial cross-section of a medical assembly according to some embodiments of the present disclosure.

FIG. 2A is a schematic diagram illustrating an exemplary medical assembly 200 according to some embodiments of the present disclosure. FIG. 2B is a schematic diagram illustrating an exemplary axial cross-section of the medical assembly 200 according to some embodiments of the present disclosure. FIG. 2C is a schematic diagram illustrating an exemplary radial cross-section of the medical assembly 200 according to some embodiments of the present disclosure. The medical assembly 200 is an exemplary embodiment of the medical assembly 111 of FIG. 1.

As shown in FIGS. 2A-2C, the medical assembly 200 may include a treatment component 210, a second imaging component 220, and a first imaging component 230. The treatment component 210 may be used to emit treatment rays to a target region of an object to provide radiotherapy on the target region. The first imaging component 230 and the second imaging component 220 may be used to perform imaging of the target region before, after, or during the radiotherapy, then, based on obtained imaging information and data, a treatment plan may be developed or adjusted, or a post-treatment evaluation of the radiotherapy may be performed. For ease of description, only a detector of the first imaging component 230 is shown in FIGS. 2A-2E.

In some embodiments, the treatment component 210 may rotate and the first imaging component 230 and the second imaging component 220 may be stationary.

In some embodiments, the treatment component 210 may include a radiation source 2101 and an annular gantry 2102. The radiation source 2101 may be disposed within an annular structure of the annular gantry 2102. The annular gantry 2102 may rotate around an object (e.g., the body of a patient) that is placed within the radiation field of the treatment component 210 to facilitate the emission of the treatment rays by the radiation source toward the target region of the object. In some embodiments, the annular gantry 2102 may rotate around an axis parallel to a length direction of a treatment bed (i.e., a $Z_2$ direction of FIGS. 2A and 2B). Further descriptions of the treatment component 210 can be found elsewhere in the present disclosure (e.g., FIG. 1 and its associated description).

In some embodiments, the annular gantry 2102 may have a hollow cannular structure. An inner annular surface of the annular gantry 2102 may form an accommodation space. The second imaging component 220 may be disposed in the accommodation space. In some embodiments, the second imaging component 220 may have a hollow cannular structure. A bore 240 may be formed by the inner annular surface of the second imaging component 220 to accommodate the object (e.g., the body of a patient) to be imaged or to be treated.

In some embodiments, the treatment component 210 and the second imaging component 220 may be coaxially disposed, i.e., a first axis of the treatment component 210 and a second axis of the second imaging component 220 may coincide. In some embodiments, an isocenter of the treatment component 210 may coincide with an isocenter of the second imaging component 220. Further description of the coincidence of the isocenters of the treatment component 210 and the second imaging component 220 can be found elsewhere in the present disclosure (e.g., FIG. 1 and its related description).

Figure 2D:
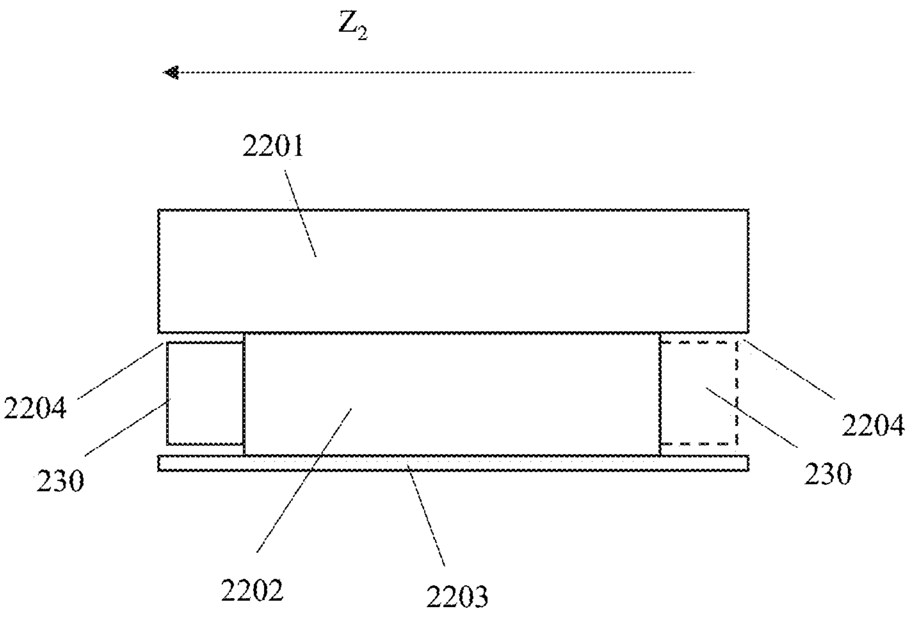
FIGS. 2D and 2E are schematic diagrams illustrating a relative position between a first imaging component and a second imaging component according to some embodiments of the present disclosure.
Figure 2E:
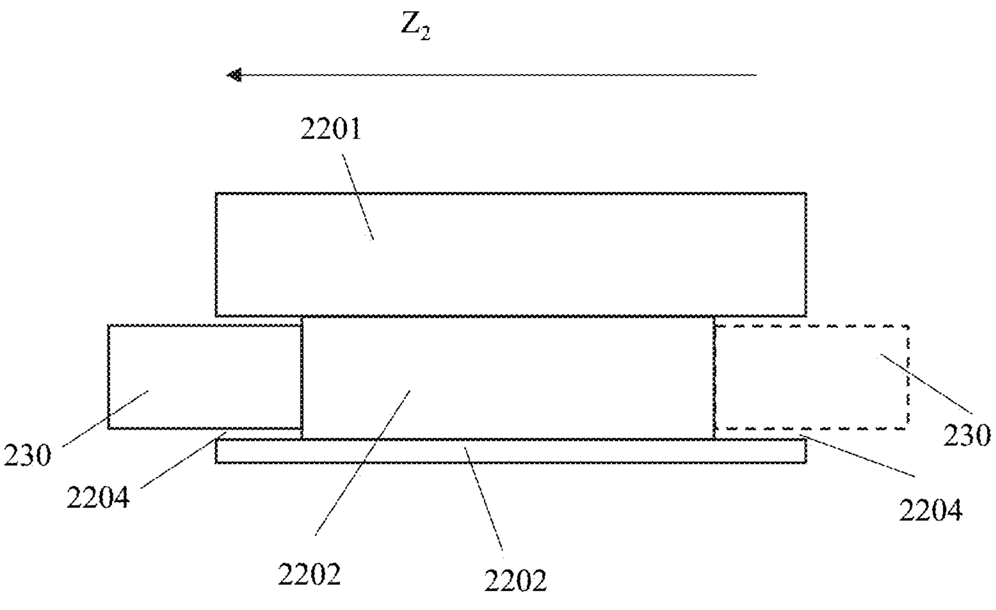

In some embodiments, the first imaging component 230 may be disposed at one end of the second imaging component 220 along an axial direction of the second imaging component 220. In some embodiments, the second imaging component 220 may include one or more unutilized hollow spaces, and at least a portion of the first imaging component 230 may be disposed in the one or more unutilized hollow spaces. For example, FIG. 2D and FIG. 2E are schematic diagrams illustrating an exemplary relative position between the first imaging component and the second imaging component according to some embodiments of the present disclosure. As shown in FIGS. 2D and 2E, in some embodiments, the second imaging component 220 may include a main magnet 2201, a gradient coil 2202, and a radio frequency coil 2203. The main magnet 2201, the gradient coil 2202, and the radio frequency coil 2203 may be disposed sequentially along a radial direction of the second imaging component 220 from an outer side to an inner side. In some embodiments, the gradient coil 2202 is disposed on an inner side of the main magnet 2201 along a radial direction of the main magnet 2201, and an axial length of the gradient coil (i.e., a $Z_2$ direction) is smaller than a length of the main magnet 2201, thus forming a hollow space 2204 on a side of the gradient coil 2202 along an axial direction of the gradient coil 2202. In some embodiments, a thickness of the gradient coil 2202 along the radial direction of the second imaging component 220 may be greater than a thickness of the first imaging component 230. Correspondingly, the first imaging component 230 may be at least partially disposed within the hollow space 2204 of the gradient coil 2202. For example, the radio frequency coil 2203 may correspond to a support cylinder and be disposed on an inner annular surface of the support cylinder, and the first imaging component 330 may be disposed on a portion of an outer annular surface of the support cylinder.

In some embodiments, as shown in FIG. 2D, the first imaging component 230 may be disposed entirely within the hollow space 2204 on one side of the gradient coil 2202 along the axial direction. In such embodiments, the first imaging component 230 may fully utilize the hollow space within the second imaging component 220, resulting in a more compact and space-saving overall structure.

In some embodiments, as shown in FIG. 2E, the first imaging component 230 may at least partially protrude out of the hollow space 2204 along an axial direction of the first imaging component 230, i.e., the first imaging component 230 may be partially disposed within the hollow space 2204 on one side of the gradient coil 2202 along the axial direction while partially protruding out of the hollow space 2204. Generally, the size of the first imaging component 230 correlates with a size of an imaging view of the first imaging component 230. When the length of the first imaging component 230 along the axial direction is short, the imaging view is small, and when the region to be imaged is large (e.g., an entire body), the small imaging view is typically not sufficient for imaging the entire region at one time, and multiple images may be required by moving the object to be imaged for multiple times, resulting in a longer imaging time and a less efficient imaging process. Accordingly, if the hollow space 2204 on one side of the gradient coil 2202 along the axial direction does not satisfy a dimensional requirement of the first imaging component 230, at least a portion of the first imaging component 230 may protrude out of the hollow space 2204 along the axial direction, i.e., the first imaging component 230 may be partially provided within the hollow space 2204 on one side of the gradient coil 2202 along the axial direction while partially protruding out of the hollow space 2204 to ensure that a size of the first imaging component 230 meets an imaging need. In some embodiments, an axial length of the first imaging component may be determined according to an actual need.

In some embodiments, a water-cooling assembly and associated cables need to be placed between the first imaging component 230 and the gradient coil 2202. As such, a distance between the first imaging component 230 and the gradient coil 2202 along the axial direction may be set according to an actual need, so as to make the distance between the first imaging component 230 and the gradient coil 2202 as small as possible while accommodating the water-cooling assembly and cables for improving space utilization.

According to some embodiments, in the medical assembly 200, at least a portion of the first imaging component 230 may be disposed in an unutilized hollow space of the second imaging component 220, which on the one hand can make full use of an internal hollow space, avoiding an overall length of the medical assembly along the axial direction being too large and saving space. On the other hand, it is possible to keep a radial dimension of the medical assembly unchanged and guarantee a larger bore size (i.e., a bore diameter of a bore 240) for imaging or treatment, which leads to a more compact overall structure, henceforth saving space and improving medical assembly applicability (e.g., the medical assembly can be applied to objects with larger sizes).

Figure 3A:
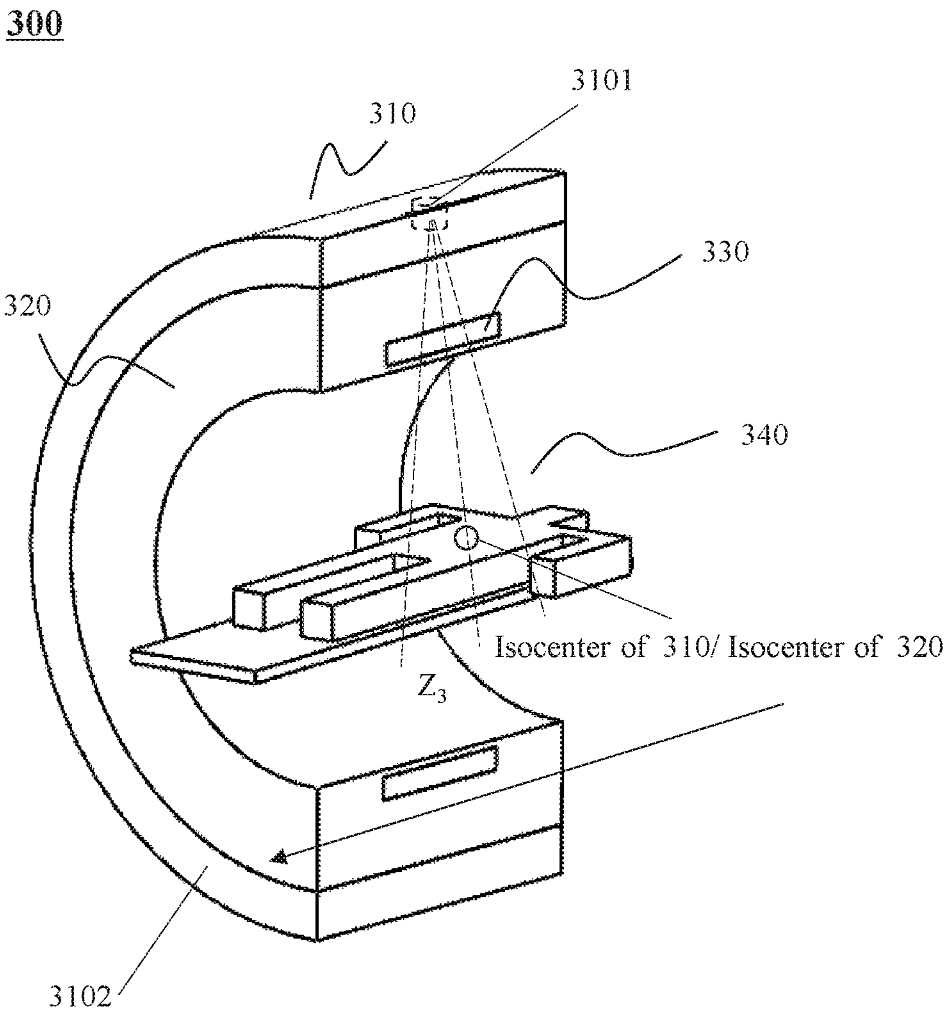
FIG. 3A is a schematic diagram illustrating an exemplary medical assembly according to some embodiments of the present disclosure.
Figure 3B:
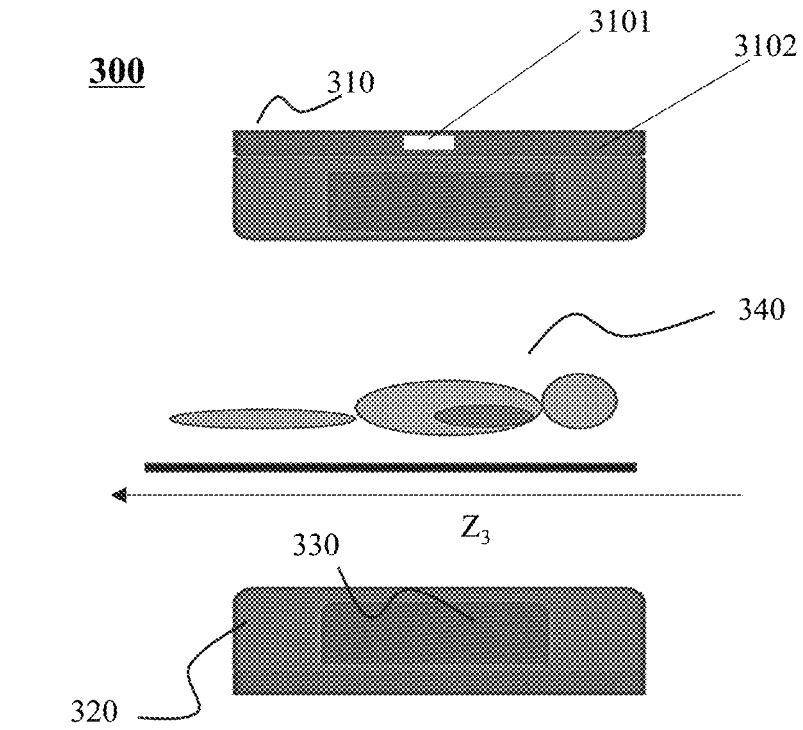
FIG. 3B is a schematic diagram illustrating an exemplary axial cross-section of a medical assembly according to some embodiments of the present disclosure.
Figure 3C:
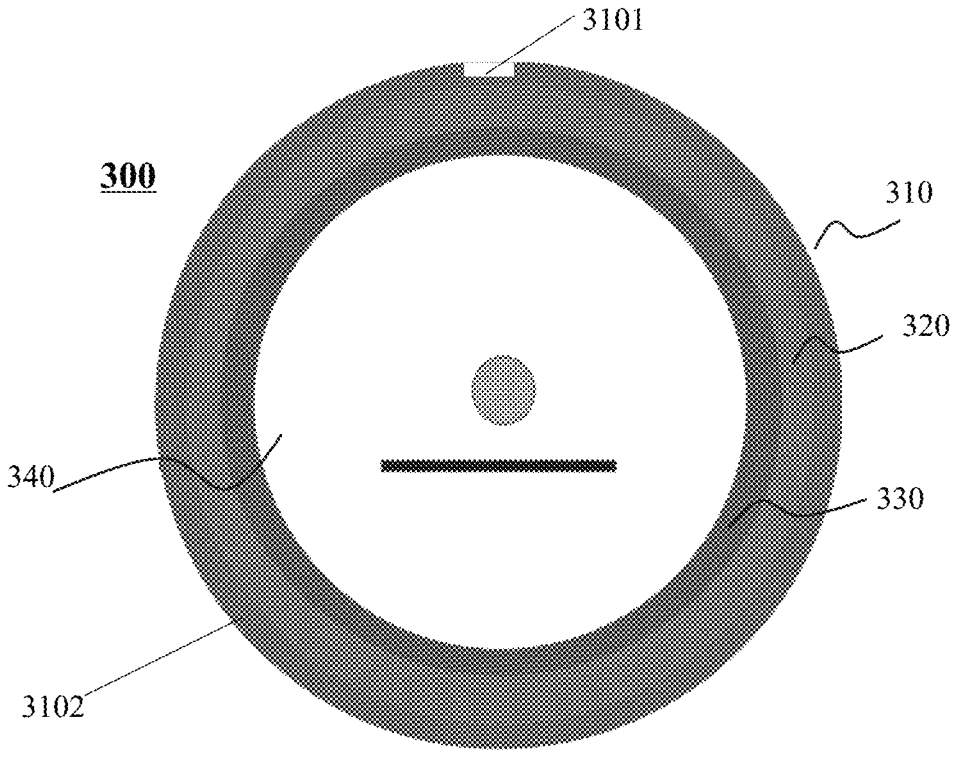
FIG. 3C is a schematic diagram illustrating an exemplary radial cross-section of a medical assembly according to some embodiments of the present disclosure.

FIG. 3A is a schematic diagram illustrating an exemplary medical assembly 300 according to some embodiments of the present disclosure. FIG. 3B is a schematic diagram illustrating an exemplary axial cross-section of the medical assembly 300 according to some embodiments of the present disclosure. FIG. 3C is a schematic diagram illustrating an exemplary radial cross-section of the medical assembly 300 according to some embodiments of the present disclosure. The medical assembly 300 is an example of the medical assembly 111 of FIG. 1.

As shown in FIGS. 3A-3C, the medical assembly 300 may include a treatment component 310, a second imaging component 320, and a first imaging component 330. The treatment component 310 may be used to emit treatment rays to a target region of an object to perform a radiotherapy on the target region. The first imaging component 330 and the second imaging component 320 may be used to perform an imaging on the target region before, after, or during the radiotherapy, then a treatment plan may be developed and adjusted or a post-evaluation of the radiotherapy may be performed based on the obtained imaging information and data. For convenience of description, only a detector of the first imaging component 330 is shown in FIGS. 3A-3E.

In some embodiments, the treatment component 310 may include a radiation source 3101 and an annular gantry 3102. The radiation source 3101 may be disposed within an annular structure of the annular gantry 3102. In some embodiments, the annular gantry 3102 may rotate around a direction parallel to a length direction of a treatment bed (i.e., a $Z_3$ direction in FIGS. 3A and 3B). In some embodiments, the annular gantry 3102 may have a hollow cannular structure. An inner annular surface of the annular gantry 3102 may form an accommodation space. The second imaging component 320 may be disposed in the accommodation space. In some embodiments, an isocenter of the treatment component 310 may coincide with an isocenter of the second imaging component 320. In some embodiments, the treatment component 310 may be the same as or similar to the treatment component 210, and the second imaging component 320 may be the same as or similar to the second imaging component 220, as described in FIGS. 2A-2C, and relevant descriptions are not be repeated herein.

Figure 3D:
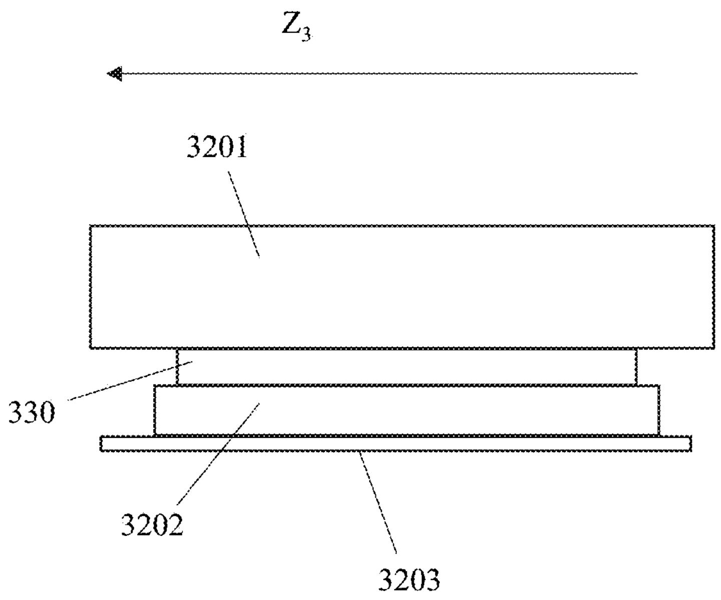
FIGS. 3D and 3E are schematic diagrams illustrating a relative position between a first imaging component and a second imaging component according to some embodiments of the present disclosure.
Figure 3E:
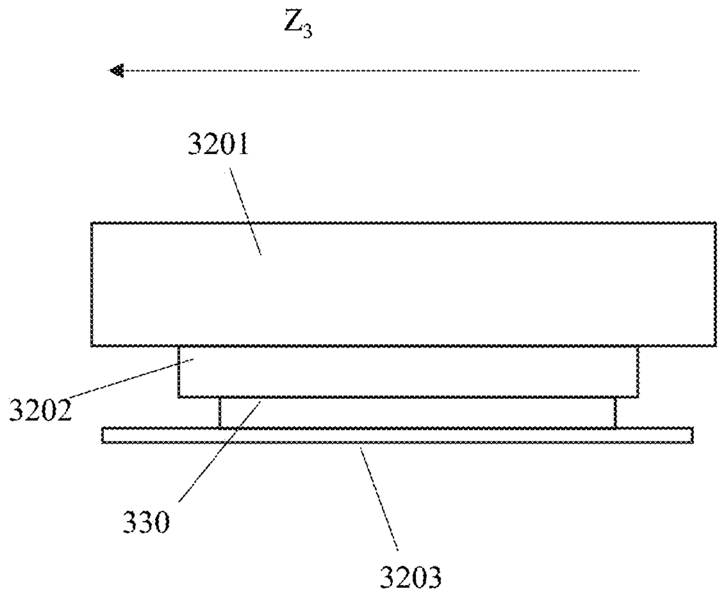

FIGS. 3D and 3E are schematic diagrams illustrating a relative position between a first imaging component and a second imaging component according to some embodiments of the present disclosure. As shown in FIGS. 3D and 3E, the second imaging component 320 may comprise a main magnet 3201, a gradient coil 3202, and a radio frequency coil 3203. The main magnet 3201, the gradient coil 3202, and the radio frequency coil 3203 may be disposed sequentially along a radial direction of the second imaging component 320 from outside to inside.

In some embodiments, as shown in FIG. 3D, the first imaging component 330 may be disposed between the main magnet 3201 and the gradient coil 3202. In some embodiments, the gradient coil 3202 may correspond to a support cylinder and be mounted on an inner annular surface of the support cylinder, and the first imaging component 330 may be disposed on an outer annular surface of the support cylinder. In some embodiments, the first imaging component 330 may be disposed on a separate support cylinder, and the support cylinder may be disposed between the main magnet 3201 and the gradient coil 3202.

In some embodiments, as shown in FIG. 3E, the first imaging component 330 may be disposed between the gradient coil 3202 and the radio frequency coil 3203. In some embodiments, the radio frequency coil 3203 may correspond to a support cylinder and be mounted on an inner annular surface of the support cylinder, and the first imaging component 330 may be disposed on an outer annular surface of the support cylinder. In some embodiments, the first imaging component 330 may be disposed on a separate support cylinder, and the support cylinder may be disposed between the gradient coil 3202 and the radio frequency coil 3203.

In some embodiments, an isocenter of the first imaging component 330 may coincide with an isocenter of the second imaging component 320. In some embodiments, an isocenter of the treatment component 310 may coincide with the isocenter of the first imaging component 330 and the isocenter of the second imaging component 320. More description regarding the isocenters can be found elsewhere in the present disclosure (e.g., FIG. 1 and its related description).

In the medical assembly 300, the first imaging component may be disposed between the gradient coil and the radio frequency coil of the second imaging component, which can effectively prevent an overall length of the medical assembly along an axial direction from being too long, thereby saving space. In addition, since an overall length of the second imaging component is relatively long and the first imaging component is disposed between the main magnet and the gradient coil or between the gradient coil and the radio frequency coil of the second imaging component, an axial length of the first imaging component may be relatively long and have a relatively large imaging view, which can better meet an imaging need, thereby eliminating the need to move an object multiple times for multiple imaging.

Figure 4A:
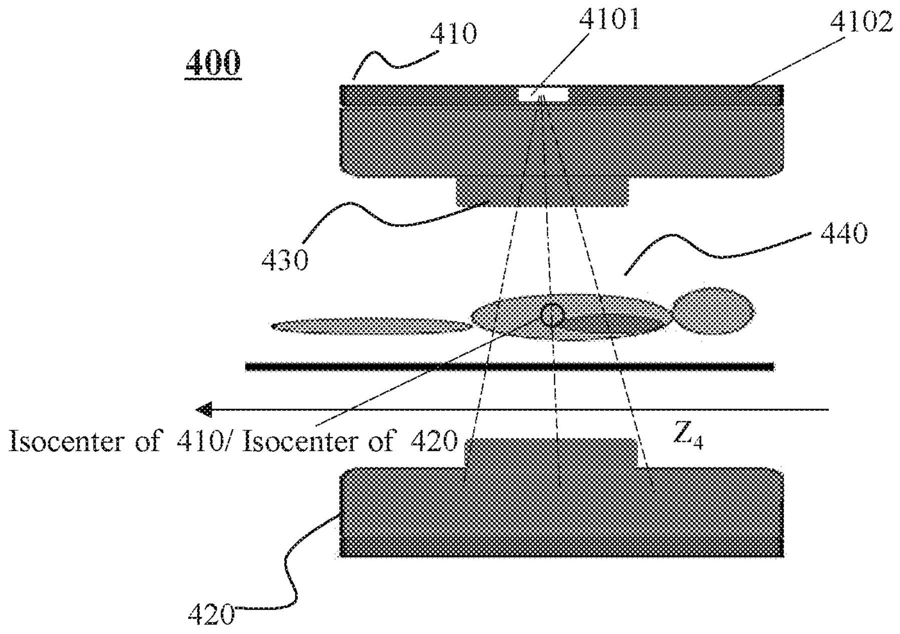
FIG. 4A is a schematic diagram illustrating an exemplary axial cross-section of a medical assembly according to some embodiments of the present disclosure.
Figure 4B:
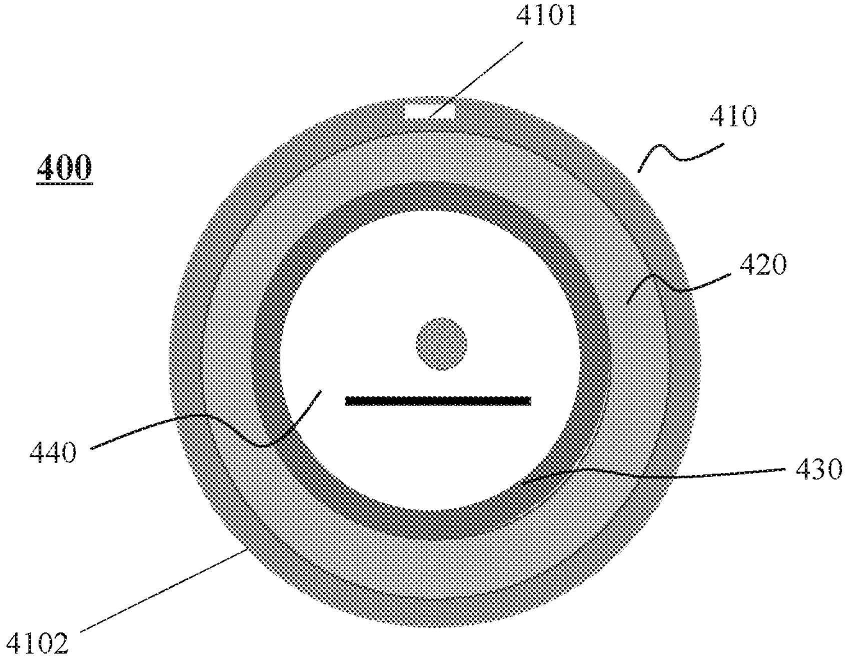
FIG. 4B is a schematic diagram illustrating an exemplary radial cross-section of a medical assembly according to some embodiments of the present disclosure.

FIG. 4A is a schematic diagram illustrating an exemplary axial cross-section of a medical assembly 400 according to some embodiments of the present disclosure. FIG. 4B is a schematic diagram illustrating an exemplary radial cross-section of the medical assembly 400 according to some embodiments of the present disclosure. The medical assembly 400 is an exemplary embodiment of the medical assembly 111 of FIG. 1.

As shown in FIGS. 4A and 4B, the medical assembly 400 may include a treatment component 410, a second imaging component 420, and a first imaging component 430. The treatment component 410 may be used to emit treatment rays to a target region of an object to perform a radiotherapy on the target region. The first imaging component 430 and the second imaging component 420 may be used to perform an imaging on the target region before, after, or during the radiotherapy, then a treatment plan may be developed and adjusted or a post-evaluation of the radiotherapy may be performed based on the obtained imaging information. For convenience of description, only a detector of the first imaging component 430 is shown in FIGS. 4A and 4B.

In some embodiments, the treatment component 410 may include a radiation source 4101 and an annular gantry 4102. The radiation source 4101 may be disposed within an annular structure of the annular gantry 4102. In some embodiments, the annular gantry 4102 may rotate around a direction parallel to a length direction of a treatment bed (i.e., a $Z_4$ direction in FIG. 4A). In some embodiments, the annular gantry 4102 may have a hollow cannular structure. An inner annular surface of the annular gantry 4102 may form an accommodation space. The second imaging component 420 may be disposed in the accommodation space. In some embodiments, an isocenter of the treatment component 410 may coincide with an isocenter of the second imaging component 420. In some embodiments, the treatment component 410 may be the same as or similar to the treatment component 310, and the second imaging component 420 may be the same as or similar to the second imaging component 320, as described in FIGS. 3A-3C, and relevant descriptions are not be repeated herein.

In some embodiments, the first imaging component 430 may be disposed on an inner side of the second imaging component 420 along a radial direction of the second imaging component 420. In some embodiments, the first imaging component 430 may be disposed on an inner annular surface of the second imaging component 420. In some embodiments, the first imaging component 430 may be disposed on a separate support cylinder, and the support cylinder may be located on an inner side of the second imaging component 420 along the radial direction of the second imaging component 420. In some embodiments, the first imaging component 430 may be a hollow cylinder. The inner annular surface of the first imaging component 430 may form a bore 440 to accommodate an object to be imaged or to be treated.

In some embodiments, an isocenter of the first imaging component 430 may coincide with an isocenter of the second imaging component 420. In some embodiments, an isocenter of the treatment component 410 may coincide with the isocenter of the first imaging component 430 and the isocenter of the second imaging component 420. More description regarding the isocenters can be found elsewhere in the present disclosure (e.g., FIG. 1 and its related description).

Similar to the medical assembly 300, in the medical assembly 400, since the first imaging component is disposed on the inner side of the second imaging component along the radial direction of the second imaging component, an axial length of the first imaging component may be relatively long and have a relatively large imaging view, which may better meet an imaging need, thereby eliminating the need to repeatedly moving an object multiple times for multiple imaging.

Figure 5A:
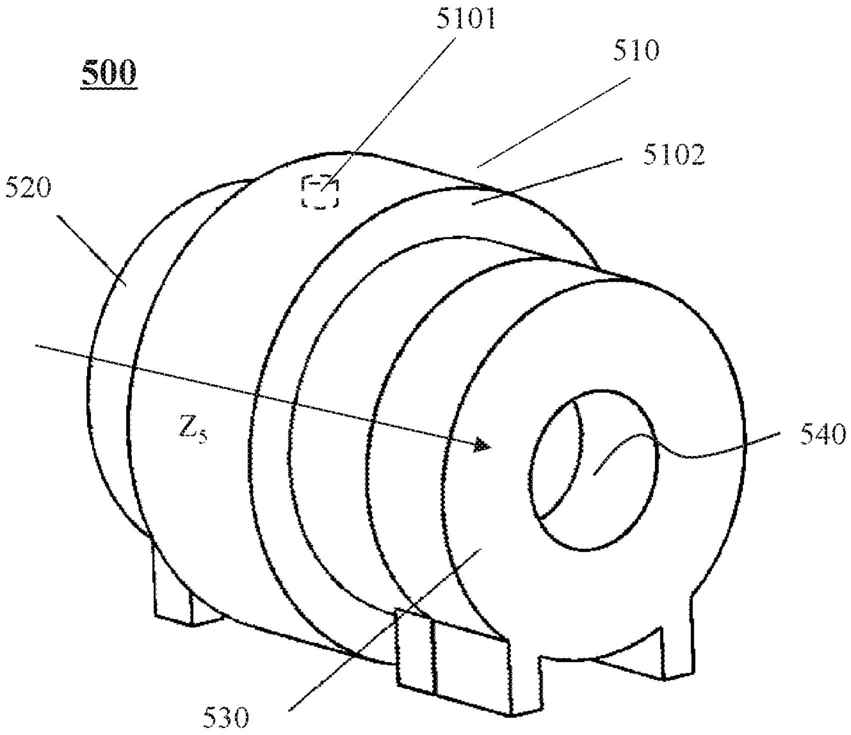
FIG. 5A is a schematic diagram illustrating an exemplary medical assembly according to some embodiments of the present disclosure.
Figure 5B:
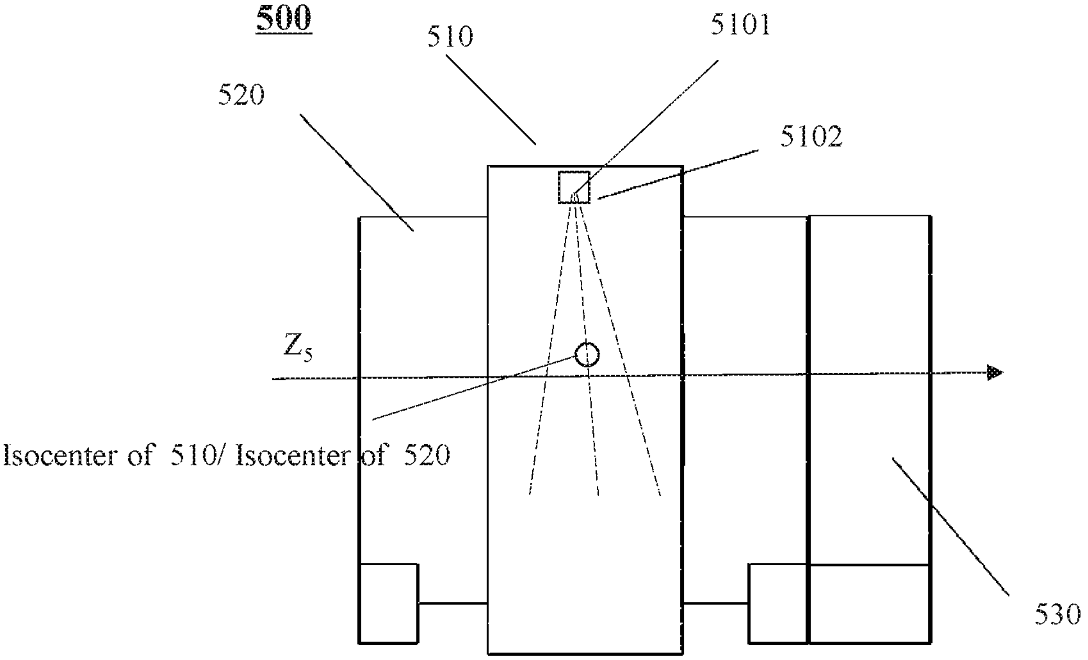
FIG. 5B is a schematic diagram illustrating an axial side view of a medical assembly according to some embodiments of the present disclosure.

FIG. 5A is a schematic diagram illustrating an exemplary medical assembly 500 according to some embodiments of the present disclosure. FIG. 5B is a schematic diagram illustrating an exemplary axial side view of the medical assembly 500 according to some embodiments of the present disclosure. In some embodiments, the medical assembly 500 is an example of the medical assembly 111 of FIG. 1.

As shown in FIGS. 5A and 5B, the medical assembly 500 may include a treatment component 510, a second imaging component 520, and a first imaging component 530. The treatment component 510 may be used to emit treatment rays to a target region of an object to perform a radiotherapy on the target region. The first imaging component 530 and the second imaging component 520 may be used to perform an imaging on the target region before, after, or during the radiotherapy, then a treatment plan may be developed and adjusted or a post-evaluation of the radiotherapy may be performed based on the obtained imaging information and data.

In some embodiments, the treatment component 510 may include an annular gantry and a radiation source disposed on the annular gantry. The radiation source 5101 may be disposed within an annular structure of the annular gantry 5102. In some embodiments, the annular gantry 5102 may rotate around a direction parallel to a length direction of a treatment bed (i.e., a $Z_5$ direction in FIGS. 5A and 5B). In some embodiments, the annular gantry 5102 may have a hollow cannular structure. An inner annular surface of the annular gantry 5102 may form an accommodation space. The second imaging component 520 may be disposed in the accommodation space. In some embodiments, an isocenter of the treatment component 510 may coincide with an isocenter of the second imaging component 520. In some embodiments, the treatment component 510 may be the same as or similar to the treatment component 210, and the second imaging component 520 may be the same as or similar to the second imaging component 220, as described in FIGS. 2A-2C, and relevant descriptions are not be repeated herein.

In some embodiments, the first imaging component 530 may be disposed adjacent to the second imaging component 520 along an axial direction (i.e., the $Z_5$ direction shown in FIGS. 5A and 5B). The first imaging component 530 is deemed as being adjacent to the second imaging component 520 along the axial direction when there is no other component between the first imaging component 530 and the second imaging component 520 along the axial direction. In some embodiments, the first imaging component 530 may include a gantry and a detector assembly, and the detector assembly may be disposed within the gantry. The gantry of the first imaging component 530 may be disposed adjacent to the second imaging component 520. In some embodiments, a distance between the first imaging component 530 and the second imaging component 520 along the axial direction may be smaller than a distance threshold (e.g., 1 cm, 5 mm, etc.), so to reduce a length of the medical assembly 500 along the axial direction.

In some embodiments, the first imaging component 530 and the second imaging component 520 are both hollow cannular structures. Inner annular surfaces of the first imaging component 530 and the second imaging component 520 may form a bore 540 along the axial direction. In some embodiments, a diameter of a bore formed by an inner annular surface of the first imaging component 530 and a diameter of a bore formed by an inner annular surface of the second imaging component 520 may be the same or different. That is, a diameter of the bore 540 may vary along the axial direction. In some embodiments, an object placed in the bore 540 may be moved to an imaging region of the first imaging component 530, an imaging region of the second imaging component 520, or a therapeutic region of the treatment component 510 to perform an imaging or a radiotherapy according to an actual need.

In some embodiments, the first imaging component 530 and the second imaging component 520 may be coaxially disposed, i.e., an axis of the first imaging component 530 may coincide with an axis of the second imaging component 520, so as to facilitate moving the object between the imaging region of the first imaging component 530 and the imaging region of the second imaging component 520, and/or the therapeutic region of the treatment component 510.

The medical assembly 500 may integrate the first imaging component, the second imaging component, and the treatment component in a single design. When it is necessary to use the first imaging component and the second imaging component at the same time to determine the target region, a time interval between an imaging performed the first imaging component and the second imaging component for performing imaging can be shortened, thereby obtaining a more accurate target region and realizing a more accurate radiotherapy.

Figure 6A:
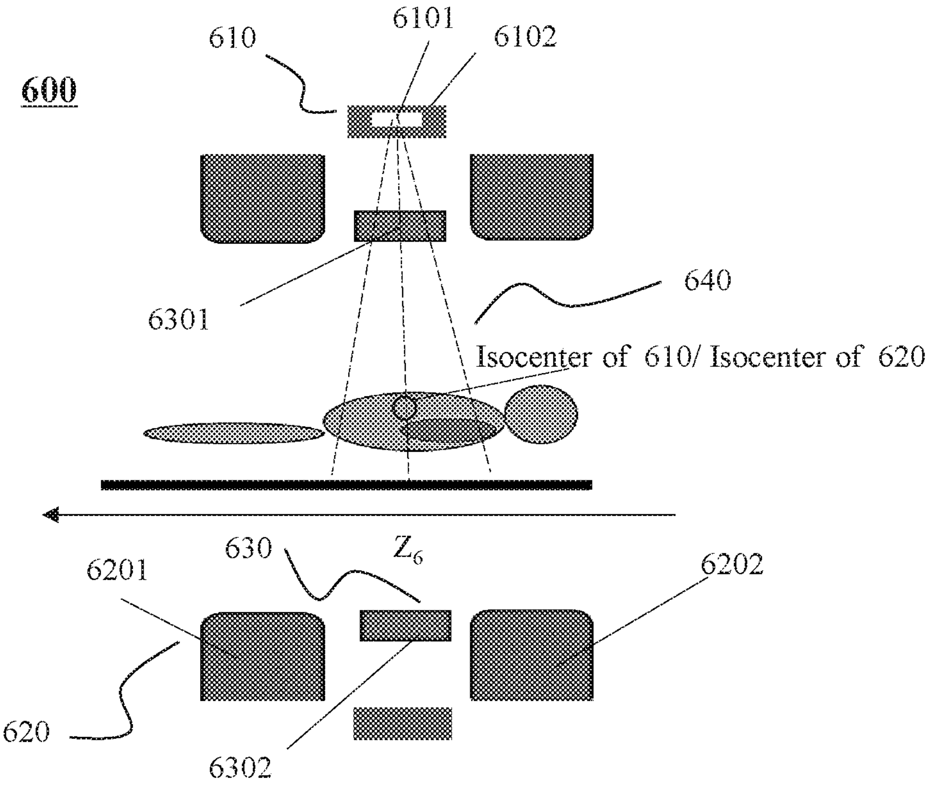
FIG. 6A is a schematic diagram illustrating an exemplary axial cross-section of a medical assembly according to some embodiments of the present disclosure.
Figure 6B:
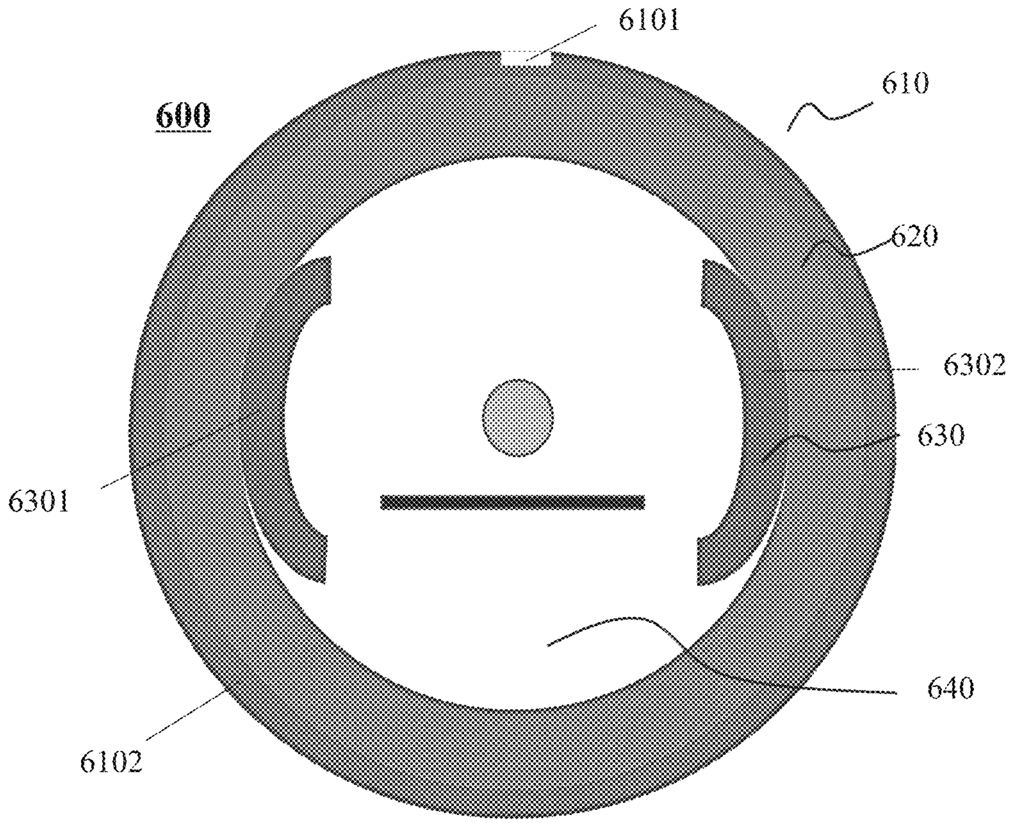
FIG. 6B is a schematic diagram illustrating a radial side view of a medical assembly according to some embodiments of the present disclosure.

FIG. 6A is a schematic diagram illustrating an exemplary axial cross-section of a medical assembly 600 according to some embodiments of the present disclosure. FIG. 6B is a schematic diagram illustrating an exemplary radial side view of the medical assembly 600 according to some embodiments of the present disclosure. In some embodiments, the medical assembly 600 is an example of the medical assembly 111 of FIG. 1.

As shown in FIGS. 6A and 6B, the medical assembly 600 may include a treatment component 610, a second imaging component 620, and a first imaging component 630. The treatment component 610 may be used to emit treatment rays to a target region of an object to perform a radiotherapy on the target region. The first imaging component 630 and the second imaging component 620 may be used to perform an imaging on the target region before, after, or during the radiotherapy, then a treatment plan may be developed or adjusted or a post-evaluation of the radiotherapy may be performed based on the obtained imaging information and data. For convenience of description, only a detector of the first imaging component 630 is shown in FIGS. 6A and 6B.

In some embodiments, the second imaging component 620 may include a first portion 6201 and a second portion 6202. In some embodiments, each of the first portion 6201 and the second portion 6202 may include a main magnet, a gradient coil, and a radio frequency coil. In some embodiments, the first portion 6201 and the second portion 6202 may have a hollow cannular structure that are set coaxially. Inner annular surfaces of the first portion 6201 and the second portion 6202 may form with a bore 640 to accommodate an object to be imaged or to be treated.

In some embodiments, at least one of the treatment component 610 or the first imaging component 630 may be disposed between the first portion 6201 and the second portion 6202. For example, as shown in FIG. 6A, the treatment component 610 and the first imaging component 630 may be disposed between the first portion 6201 and the second portion 6202.

In some embodiments, the treatment component 610 may include a radiation source 6101 and an annular gantry 6102. The radiation source 6101 may be disposed within an annular structure of the annular gantry 6102. The annular gantry 6102 may rotate around an object (e.g., a patient) that is moved into a radiation field of the treatment component 610 to facilitate emitting the treatment rays into the target region of the object. In some embodiments, the annular gantry 6102 may rotate around a direction parallel to a length direction of a treatment bed (i.e., a $Z_6$ direction in FIG. 6A). More description of the treatment component 610 can be found elsewhere in the present disclosure (e.g., FIG. 1 and its related description).

In some embodiments, the treatment component 610, the first portion 6201, and the second portion 6202 may be coaxially provided. In some embodiments, an isocenter of the treatment component 610 may coincide with an isocenter of the second imaging component 620. More descriptions regarding the coincidence of the isocenters of the treatment component 610 and the second imaging component 620 can be found elsewhere in the present disclosure (e.g., FIG. 1 and its related description).

In some embodiments, the first imaging component 630 may be disposed on an inner side of the annular gantry 6102. In some embodiments, the first imaging component 630 may have a hollow cannular structure. An inner annular surface of the first imaging component 630 may form a bore 640 to accommodate an object to be imaged or to be treated. In some embodiments, the first imaging component 630 may be stationary. For example, the first imaging component 630 may be immobilized on a floor, on the treatment bed, or on the second imaging component 620.

In some embodiments, the first imaging component 630 may include a first portion 6301 and a second portion 6302. In some embodiments, the first portion 6301 and the second portion 6302 may be disposed relative to each other with respect to the radiation source 6101. Therefore, the treatment rays emitted by the radiation source 6101 does not irradiate the first imaging component 630, thereby reducing the radiation impact of the rays emitted by the radiation source 6101 on the first imaging component 630.

In some embodiments, the first portion 6301 and the second portion 6302 may be disposed symmetrically with respect to a length direction of a treatment bed (i.e., a $Z_6$ direction of FIG. 6A). For example, as shown in FIG. 6A, the first portion 6301 and the second portion 6302 may be disposed symmetrically up and down with respect to the length direction of the treatment bed. As another example, as shown in FIG. 6B, the first portion 6301 and the second portion 6302 may be disposed symmetrically left and right with respect to the length direction of the treatment bed. The present disclosure is not limited herein. In some embodiments, the first portion 6301 and the second portion 6302 may have a circular structure.

In some embodiments, the first portion 6301 and the second portion 6302 of the first imaging component 630 may rotate in synchronization with the radiation source 6101 to keep a relative position of the first portion 6301 and the second portion 6302 of the first imaging component 630 with respect to the radiation source 6101 unchanged. In some embodiments, the first portion 6301 and the second portion 6302 of the first imaging component 630 may be disposed on an inner annular surface of the annular gantry 6102, and when the radiation source 6101 rotates as the annular gantry 6102 rotates, the first portion 6301 and the second portion 6302 of the first imaging component 630 rotate in synchronization, so as to maintain a relative position of the first portion 6301 and the second portion 6302 with respect to the radiation source 6101 unchanged. In some embodiments, the first portion 6301 and the second portion 6302 of the first imaging component 630 may be provided in separate rotating gantries. The rotating gantry and the annular gantry 6102 may rotate in synchronization to maintain the relative position of the first portion 6301 and the second portion 6302 of the first imaging component 630 with respect to the radiation source 6101 unchanged. For example, the rotating gantry and the annular gantry 6102 may be synchronized to rotate via a locking structure to keep the relative position of the first portion 6301 and the second portion 6302 of the first imaging component 630 with respect to the radiation source 6101 unchanged. For example, a synchronized rotation may be achieved by setting rotational speeds of the rotating gantry and the annular gantry 6102, so as to keep the relative position of the first portion 6301 and the second portion 6302 of the first imaging component 630 with respect to the radiation source 6101 unchanged.

In some embodiments, the first portion 6301 and the second portion 6302 of the first imaging component 630 may be disposed on at least one slip ring. In some embodiments, the first portion 6301 and the second portion 6302 of the first imaging component 630 may be disposed on two slip rings that are symmetrical with respect to the annular gantry 6102, so that the first portion 6301 and second portion 6302 of the first imaging component 630 can be supported more stably.

In some embodiments, the first portion 6301 and the second portion 6302 of the first imaging component 630 may be moved along a plurality of directions so that a region to be imaged of the object may be located in a center of an imaging area of the first imaging component 630, thus improving the quality of the imaging. For example, the first portion 6301 and the second portion 6302 of the first imaging component 630 may be moved so that an imaging center point of the first imaging component 630 coincides with a center point of the region to be imaged of the object.

In some embodiments, the treatment component 610, the second imaging component 620, and the first imaging component 630 may be coaxially disposed. In some embodiments, an isocenter of the first imaging component 630 may coincide with an isocenter of the second imaging component 620. In some embodiments, an isocenter of the treatment component 610 coincides with the isocenter of the first imaging component 630 and the isocenter of the second imaging component 620. More description regarding the isocenters can be found elsewhere in the present disclosure (e.g., FIG. 1 and its related description).

In the medical assembly 600, the first imaging component comprises two portions that are symmetrically disposed with respect to the radiation source of the treatment component. Accordingly, as the two portions of the first imaging component rotate by a certain angle, a complete imaging function along the radial direction can be realized, and at the same time, the radiation effect of the treatment rays on the first imaging component can be reduced.

Figure 7A:
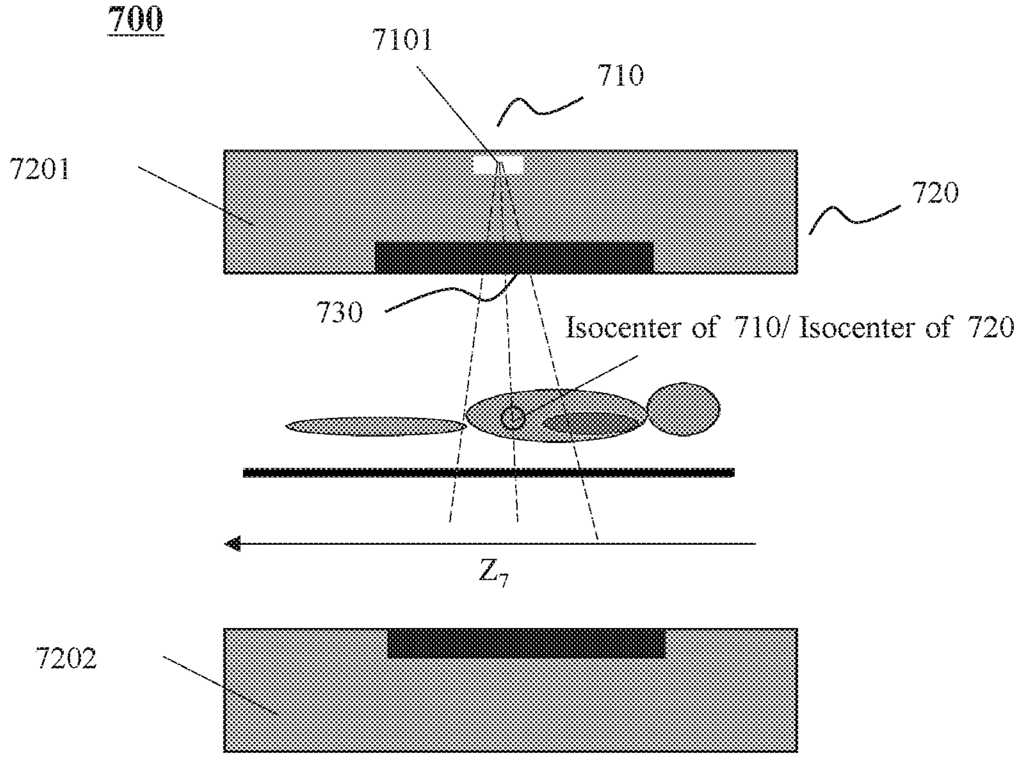
FIG. 7A is a schematic diagram illustrating an axial cross-section of a medical assembly according to some embodiments of the present disclosure.
Figure 7B:
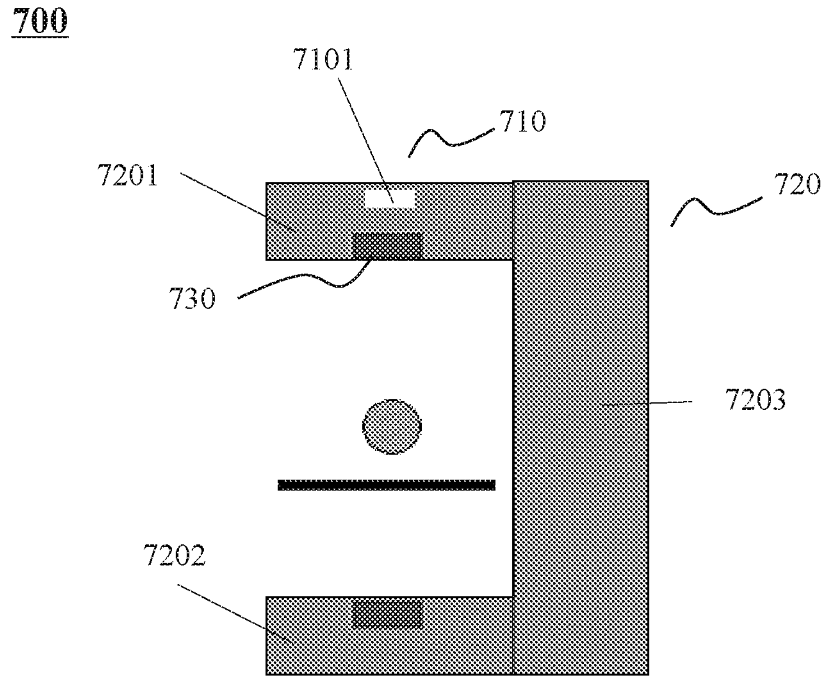
FIG. 7B is a schematic diagram illustrating a radial side view of a medical assembly according to some embodiments of the present disclosure.
Figure 7C:
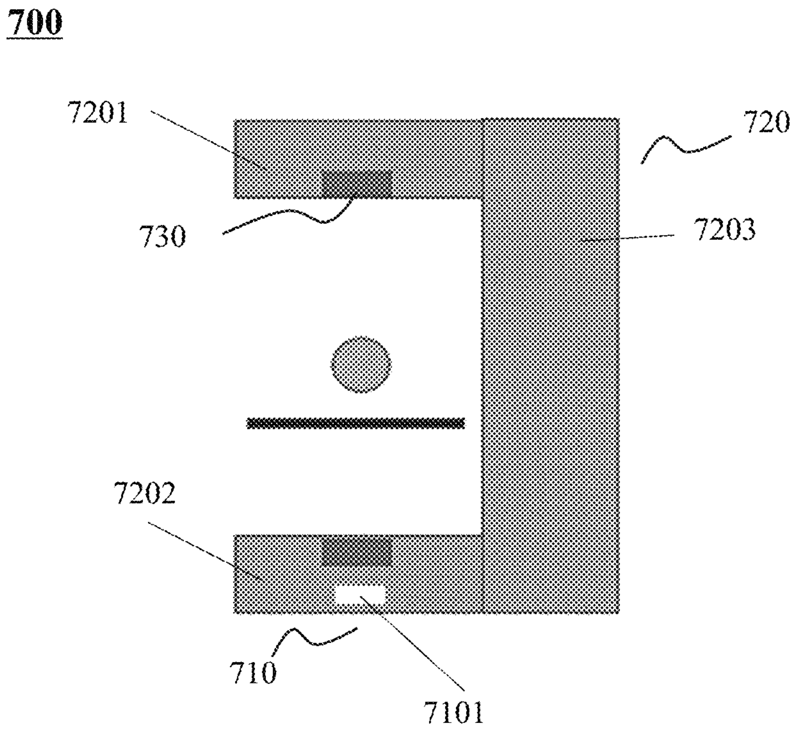
FIG. 7C is a schematic diagram illustrating a radial side view of a medical assembly according to some embodiments of the present disclosure.
Figure 7D:
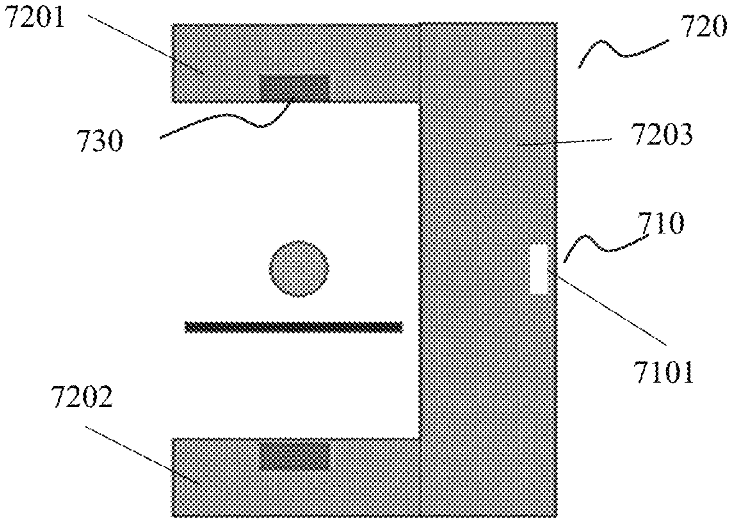
FIG. 7D is a schematic diagram illustrating a radial side view of a medical assembly according to some embodiments of the present disclosure.

FIG. 7A is a schematic diagram illustrating an exemplary axial cross-section view of a medical assembly 700 according to some embodiments of the present disclosure. FIG. 7B is a schematic diagram illustrating an exemplary radial side view of the medical assembly 700 according to some embodiments of the present disclosure. FIG. 7C is a schematic diagram illustrating an exemplary radial side view of the medical assembly 700 according to some embodiments of the present disclosure. FIG. 7D is a schematic diagram illustrating an exemplary radial side view of the medical assembly 700 according to some embodiments of the present disclosure. In some embodiments, the medical assembly 700 is an example of the medical assembly 111 of FIG. 1.

As shown in FIGS. 7A-7D, the medical assembly 700 may include a treatment component 710, a second imaging component 720, and a first imaging component 730. The treatment component 710 may be used to emit treatment rays to a target region of an object to perform a radiotherapy on the target region. The first imaging component 730 and the second imaging component 720 may be used to perform an imaging on the target region before, after, or during the radiotherapy, then a treatment plan may be developed and adjusted, or a post-evaluation of the radiotherapy may be performed based on the obtained imaging information and data.

In some embodiments, the second imaging component 720 may include a first portion 7201, a second portion 7202, and a third portion 7203. The third portion 7203 may be used to connect the first portion 7201 and the second portion 7202. The first portion 7201 and the second portion 7202 are disposed opposite to each other and are disposed at opposite ends of the third portion 7203, respectively. An accommodation space may be formed between the first portion 7201 and the second portion 7202 to accommodate an object to be imaged or to be treated. In some embodiments, the second imaging component 720 may rotate around a direction parallel to a length direction of a treatment bed (i.e., a $Z_7$ direction in FIG. 7B).

In some embodiments, an isocenter of the treatment component 710 may coincide with an isocenter of the second imaging component 720. More description regarding the coincidence of the isocenters of the treatment component 710 and the second imaging component 720 can be found elsewhere in the present disclosure (e.g., FIG. 1 and its related description). In some embodiments, the treatment component 710 may include a radiation source 7101. In some embodiments, the radiation source 7101 of the treatment component 710 may be disposed on the second imaging component 720.

In some embodiments, as shown in FIGS. 7A and 7B, the radiation source 7101 may be disposed on the first portion 7201 of the second imaging component 720. For example, the radiation source 7101 may be disposed on a side surface of the first portion 7201 of the second imaging component 720 away from the second portion 7202. As another example, the radiation source 7101 may be disposed on a side face of the first portion 7201 of the second imaging component 720 facing the second portion 7202. Furthermore, for example, the radiation source 7101 may be disposed within the first portion 7201 of the second imaging component 720.

In some embodiments, as shown in FIG. 7C, the radiation source 7101 may be disposed on the second portion 7202 of the second imaging component 720. For example, the radiation source 7101 may be disposed on a side surface of the second portion 7202 of the second imaging component 720 away from the first portion 7201. As another example, the radiation source 7101 may be disposed on a side face of the second portion 7202 of the second imaging component 720 facing the first portion 7201. Furthermore, for example, the radiation source 7101 may be disposed within the second portion 7202 of the second imaging component 720.

In some embodiments, as shown in FIG. 7D, the radiation source 7101 may be disposed on the third portion 7203 of the second imaging component 720. For example, the radiation source 7101 may be disposed on a side surface of the third portion 7203 of the second imaging component 720 away from the first portion 7101 and the second portion 7202. As another example, the radiation source 7101 may be disposed on a side surface of the third portion 7203 of the second imaging component 720 facing the first portion 7101 and the second portion 7202. Further example, the radiation source 7101 may be disposed within the third portion 7203 of the second imaging component 720.

In some embodiments, the first imaging component 730 may be disposed on the second imaging component 720. For example, the first imaging component 730 may include two portions that are disposed on the first portion 7201 and the second portion 7202 of the second imaging component 720, respectively. The two portions of the first imaging component 730 may be disposed symmetrically with respect to an axis of the second imaging component 720.

In some embodiments, the isocenter of the treatment component 710 may coincide with an isocenter of the first imaging component 730 and the isocenter of the second imaging component 720. More description regarding the isocenters can be found in other portions of the present disclosure (e.g., FIG. 1 and its related description).

In the medical assembly 700, a ray source of the treatment component is directly located on the second imaging component without a gantry, which saves costs and can effectively prevent a radial length of the medical assembly from being too long. The first imaging component is directly disposed on the second imaging component, which can effectively prevent the overall length of the medical assembly along an axial direction from being too long to save space.

Figure 8:
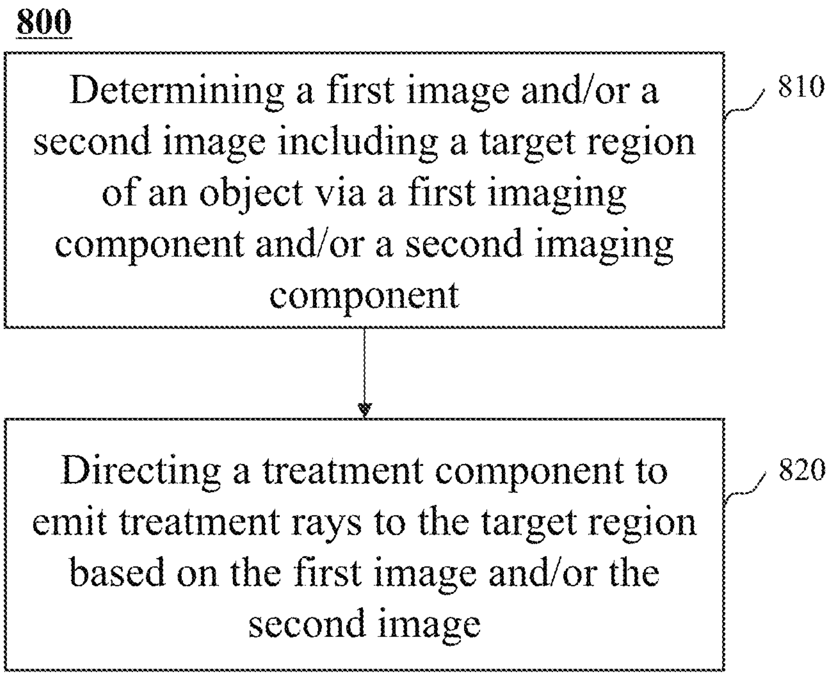
FIG. 8 is a flowchart illustrating an exemplary radiotherapy process according to some embodiments of the present disclosure.

FIG. 8 is a flowchart illustrating an exemplary process of a radiotherapy according to some embodiments of the present disclosure. A process 800 may be performed by the radiotherapy system 100. For example, the process 800 may be stored as instructions (e.g., an application program) in the storage device 150 and invoked and/or executed by the processing device 140. In some embodiments, one or more operations of the process 800 may be performed with manual intervention. The operations of the process shown below are illustrative only and do not intend to limit the present disclosure.

In operation 810, the processing device 140 may determine a first image and/or a second image including a target region of an object via a first imaging component and/or a second imaging component.

In some embodiments, the object may include a patient or a portion thereof (e.g., head, breast, abdomen, etc.). In some embodiments, the target region may refer to a region that needs to receive the radiotherapy. The target region may include cells, a tissue, an organ (e.g., a lung, a brain, a spine, a liver, a pancreas, a breast, etc.), etc., or any combination thereof. In some embodiments, the target region may be a tumor, an organ comprising a tumor, tissue comprising a tumor, or the like.

In some embodiments, the first image and/or the second image may be a two-dimensional (2D) image, a three-dimensional (3D) image, a four-dimensional (4D) image, or the like.

In some embodiments, the processing device 140 may obtain first imaging data via the first imaging component and determine the first image based on the first imaging data. In some embodiments, the processing device 140 may obtain second imaging data via the second imaging component and determine the second image based on the second imaging data. In some embodiments, the processing device 140 may use one or more reconstruction algorithms to determine the first image and/or the second image based on the first imaging data and/or second imaging data obtained. Exemplary reconstruction algorithms may include an iterative reconstruction algorithm (e.g., a statistical reconstruction algorithm), a Fourier Slice Theorem algorithm, a filtered inverse projection algorithm, a fan-beam reconstruction algorithm, an analytical reconstruction algorithm, etc., or any combination thereof.

In operation 820, the processing device 140 may direct a treatment component to emit treatment rays toward the target region based on the first image and/or the second image.

In some embodiments, the processing device 140 may determine a first target region in the first image and/or a second target region in the second image. In some embodiments, the processing device 140 may determine the first target region in the first image and/or the second target region in the second image based on one or more image segmentation algorithms. Exemplary image segmentation algorithms may include thresholding algorithms, region growing algorithms, energy function based algorithms, level set algorithms, region splitting and/or merging, edge tracking segmentation algorithms, statistical pattern recognition algorithms, mean clustering segmentation algorithms, modeling algorithms, deformable model-based segmentation algorithms, artificial neural network methods, minimum path segmentation algorithms, tracking algorithms, rule-based segmentation algorithms, coupled surface segmentation algorithms, or the like, or any combination thereof.

In some embodiments, the processing device 140 may determine a final target region based on the first target region and the second target region. In some embodiments, the processing device 140 may designate the first target region or the second target region as the final target region. In some embodiments, the processing device 140 may determine the final target region by fusing, matching, etc. the first target region and the second target region.

In some embodiments, prior to the radiotherapy, the processing device 140 or a user (e.g., a physician) may develop a treatment plan (e.g., a radiation dose) for the target region based on the first image and/or the second image. In some embodiments, the processing device 140 may also determine whether an adjustment to the treatment plan is needed based on a determined target region (e.g., size or location of the target region, etc.). In some embodiments, the processing device 140 may also determine whether the adjustment to the treatment plan is needed by combining basic information about the object (e.g., body size, weight).

In some embodiments, the processing device 140 may locate the target region. In some embodiments, the processing device 140 may match the target region to a therapeutic region of the treatment component. In some embodiments, the processing device 140 may position a center of the target region at an isocenter of the treatment component.

In some embodiments, the isocenter of the treatment component coincides with an isocenter of the second imaging component. Correspondingly, the therapeutic region of the treatment component at least partially overlaps with an imaging region of the second imaging component. The processing device 140 may locate the target region in this overlapping region.

In some embodiments, after the positioning of the target region is complete, the processing device 140 may enable a radiation source of the treatment component to emit treatment rays toward the target region of the object to treat the target region. In some embodiments, movement of one or more organs in or near the target region of the object may cause change in the location of the target region. Movement of the one or more organs may include heart movement, respiratory movement, blood flow, bladder movement, or the like, or any combination thereof. During a treatment process, since the isocenter of the treatment component coincides with the isocenter of the second imaging component, the processing device 140 may track the treatment process in real time through the second imaging component so as to provide timely feedback on change of the target region, adjust the treatment plan or interrupt radiation if necessary, thereby effectively improving the precision and speed of the treatment process, and minimizing damage to the healthy tissues of the patient while ensuring that a sufficient radiation dose is irradiated upon the target region. For example, the processing device 140 may determine an in-treatment image of the target region of the object via the second imaging component. During the treatment process, the processing device 140 may monitor the change in the target region based on the in-treatment image and determine how to proceed with subsequent radiotherapy based on the monitoring result, and a subsequent step may include continuing radiotherapy as originally scheduled, adjusting the treatment plan, or terminating the treatment.

In some embodiments, an isocenter of the first imaging component may coincide with the isocenter of the second imaging component, and the isocenter of the treatment component. Correspondingly, the therapeutic region of the treatment component, the imaging region of the first imaging component, and the imaging region of the second imaging component at least partially overlap. The processing device 140 may locate the target region in this overlapping region. During the treatment, the processing device 140 may track the treatment process via both the first imaging component and the second imaging component to monitor the change of the target region more accurately.

In some embodiments, the processing device 140 may send a monitoring image of the treatment process to the terminal device 130. The user may determine a subsequent treatment plan based on the monitoring image and send relevant instructions to the processing device 140. The subsequent treatment plan may include continuing radiotherapy as originally planned, adjusting the treatment plan, or terminating the treatment.

In some embodiments, after completion of the treatment, the processing device 140 may image the target region via the first imaging component and/or the second imaging component to obtain post-treatment imaging data. The processing device 140 or the user (e.g., a physician) may perform a post-treatment evaluation of the target region based on the post-treatment imaging data.

In some embodiments, the processing device 140 or the user (e.g., a physician) may determine whether a next treatment is needed for the target region based on an evaluation result obtained from the post-treatment evaluation. If it is determined that the next treatment is needed, the processing device 140 or the user (e.g., a physician) may develop a plan for the next treatment based on the evaluation result obtained from the post-treatment evaluation. If it is determined that the next treatment is not needed, the processing device 140 may decide to terminate the treatment.

It should be noted that the foregoing description of the process 800 is intended to be exemplary and illustrative only and does not limit the scope of application of the present disclosure. For a person skilled in the art, various corrections and changes can be made to the process 800 under the guidance of the present disclosure. However, these corrections and changes remain within the scope of the present disclosure. In some embodiments, the process 800 may include one or more other operations. For example, the process 800 may include an operation of determining the treatment plan by the first imaging component and/or the second imaging component. As another example, the process 800 may include an operation of determining whether the adjustment to the treatment is needed based on the first image and/or the second image. Furthermore, for example, the process 800 may include an operation of performing the post-treatment evaluation of the target region by the first imaging component and/or the second imaging component after completion of the treatment.

The basic concepts have been described above, and it is apparent to those skilled in the art that the foregoing detailed disclosure is intended as an example only and does not constitute a limitation of the present disclosure. While not expressly stated herein, a person skilled in the art may make various modifications, improvements, and amendments to the present disclosure. Those types of modifications, improvements, and amendments are suggested in the present disclosure, so those types of modifications, improvements, and amendments remain within the spirit and scope of the exemplary embodiments of the present disclosure.

Also, the present disclosure uses specific words to describe embodiments of the present disclosure Words such as “an embodiment”, “one embodiment”, and/or “some embodiment” means a feature, structure, or characteristic associated with at least one embodiment of the present disclosure. Accordingly, it should be emphasized and noted that “an embodiment”, “one embodiment”, or “an alternative embodiment” referred to two or more times in different locations in the present disclosure do not necessarily refer to the same embodiment. In addition, certain features, structures, or characteristics in one or more embodiments of the present disclosure may be suitably combined.

Furthermore, unless expressly stated in the claims, the order of the processing elements and sequences described herein, the use of numerical letters, or the use of other names are not intended to qualify the order of the processes and methods of the present disclosure. While some embodiments of the invention that are currently considered useful are discussed in the foregoing disclosure by way of various examples, it is to be understood that such details serve only illustrative purposes and that additional claims are not limited to the disclosed embodiments, rather, the claims are intended to cover all amendments and equivalent combinations that are consistent with the substance and scope of the embodiments of the present disclosure.

Similarly, it should be noted that in order to simplify the presentation of the disclosure of the present disclosure, and thereby aid in the understanding of one or more embodiments of the invention, the foregoing descriptions of embodiments of the present disclosure sometimes group multiple features together in a single embodiment, accompanying drawings, or a description thereof. However, this method of disclosure does not imply that the objects of the present disclosure require more features than those mentioned in the claims.

Some embodiments use numbers describing the number of components, attributes, and it is to be understood that such numbers used in the description of embodiments are modified in some examples by the modifiers “about”, “approximately”, or “substantially”. Unless otherwise noted, the terms “about,” “approximate,” or “substantially” indicates that a ±20% variation in the stated number is allowed. Correspondingly, in some embodiments, the numerical parameters used in the present disclosure and claims are approximations, which approximations are subject to change depending on the desired characteristics of individual embodiments. In some embodiments, the numerical parameters should take into account the specified number of valid digits and employ general place-keeping. While the numerical domains and parameters used to confirm the breadth of their ranges in some embodiments of the present disclosure are approximations, in specific embodiments, such values are set to be as precise as possible within the feasible range.

For each patent, patent application, patent application disclosure, and other material cited in the present disclosure, such as articles, books, specification sheets, publications, documents, etc., the entire contents of which are hereby incorporated herein by reference. Except for application history documents that are inconsistent with or create a conflict with the contents of the present disclosure, and except for documents that limit the broadest scope of the claims of the present disclosure (currently or hereafter appended to the present disclosure). It should be noted that in the event of any inconsistency or conflict between the descriptions, definitions, and/or use of terminology in the materials appended to the present disclosure and those set forth in the present disclosure, the descriptions, definitions, and/or use of terms in the present disclosure shall prevail.

Finally, it should be understood that the embodiments described herein are only used to illustrate the principles of the embodiments of the present disclosure. Other deformations may also fall within the scope of the present disclosure. As such, alternative configurations of embodiments of the present disclosure may be viewed as consistent with the teachings of the present disclosure as an example, not as a limitation. Correspondingly, the embodiments of the present disclosure are not limited to the embodiments expressly presented and described herein.

What is claimed is:

1. A radiotherapy system, comprising:

a first imaging component and a second imaging component, configured to determine a target region of an object and/or guide an emission of treatment rays, wherein the first imaging component is a positron emission computed tomography PET) device, and the second imaging component is a magnetic resonance imaging MRI) device; and a treatment component, configured to emit the treatment rays toward the target region, an isocenter of the treatment component coinciding with an isocenter of the second imaging component, wherein the treatment component includes a radiation source and an annular gantry, the radiation source is disposed within the annular gantry, an inner annular surface of the annular gantry forms an accommodation space, and the second imaging component is disposed in the accommodation space.

2. The radiotherapy system of claim 1, wherein the first imaging component is disposed at an end of the second imaging component along an axial direction of the second imaging component.

3. The radiotherapy system of claim 1, wherein the second imaging component comprises a main magnet and a gradient coil, the gradient coil is disposed on an inner side of the main magnet along a radial direction of the main magnet, an axial length of the gradient coil is smaller than an axial length of the main magnet, a hollow space is formed on a side of the gradient coil along an axial direction of the gradient coil, and the first imaging component is located within the hollow space.

4. The radiotherapy system of claim 3, wherein the first imaging component at least partially protrudes out of the hollow space along an axial direction of the first imaging component.

5. The radiotherapy system of claim 1, wherein the second imaging component comprises a gradient coil and a radio frequency coil, and the first imaging component is disposed between the gradient coil and the radio frequency coil.

6. The radiotherapy system of claim 1, wherein the first imaging component is disposed on an inner side of the second imaging component along a radial direction of the second imaging component.

7. The radiotherapy system of claim 1, wherein an isocenter of the first imaging component coincides with the isocenter of the second imaging component.

8. The radiotherapy system of claim 1, wherein the second imaging component is a hollow annular structure, and the hollow annular structure has a second axis, the first imaging component is disposed adjacent to the second imaging component along an axial direction, the axial direction referring to a direction parallel to the second axis of the second imaging component.

9. The radiotherapy system of claim 1, wherein the second imaging component includes a first portion and a second portion, and the treatment component and the first imaging component are disposed between the first portion and the second portion.

10. The radiotherapy system of claim 9, wherein the first imaging component includes two portions disposed opposite to each other with respect to a radiation source of the treatment component.

11. The radiotherapy system of claim 10, wherein the two portions of the first imaging component are movable.

12. The radiotherapy system of claim 9, wherein the first imaging component rotates in synchronization with the treatment component.

13. The radiotherapy system of claim 9, wherein an isocenter of the first imaging component coincides with the isocenter of the second imaging component.

14. The radiotherapy system of claim 1, wherein the treatment component is disposed on the second imaging component, the first imaging component is disposed within the second imaging component, and the second imaging component is rotatable.

15. The radiotherapy system of claim 1, wherein the first imaging component is disposed within the second imaging component, and the second imaging component is rotatable.

16. The radiotherapy system of claim 5, wherein the radiotherapy system further comprises a support cylinder, the radio frequency coil is mounted on an inner annular surface of the support cylinder, the first imaging component is disposed on an outer annular surface of the support cylinder, and the support cylinder is disposed between the gradient coil and the radio frequency coil.

17. The radiotherapy system of claim 1, wherein the second imaging component comprises a main magnet and a gradient coil, and the first imaging component is disposed between the gradient coil and the main magnet.

18. The radiotherapy system of claim 1, wherein an isocenter of the first imaging component does not coincide with the isocenter of the second imaging component.

19. A radiotherapy method, comprising:

determining a first image and/or a second image including a target region of an object via a first imaging component and/or a second imaging component, wherein the first imaging component is a positron emission computed tomography (PET) device, and the second imaging component is a magnetic resonance imaging (MRI) device; and directing a treatment component to emit treatment rays toward the target region based on the first image and/or the second image, an isocenter of the treatment component coinciding with an isocenter of the second imaging component, wherein the treatment component includes a radiation source and an annular gantry, the radiation source is disposed within the annular gantry, an inner annular surface of the annular gantry forms an accommodation space, and the second imaging component is disposed in the accommodation space.

20. A non-transitory computer readable medium, comprising at least one set of instructions, wherein when executed by one or more processors of a computing device, the at least one set of instructions causes the computing device to perform a method, the method comprising:

determining a first image and/or a second image including a target region of an object via a first imaging component and/or a second imaging component, wherein the first imaging component is a positron emission computed tomography (PET) device, and the second imaging component is a magnetic resonance imaging (MRI) device; and directing a treatment component to emit treatment rays toward the target region based on the first image and/or the second image, an isocenter of the treatment component coinciding with an isocenter of the second imaging component, wherein the treatment component includes a radiation source and an annular gantry, the radiation source is disposed within the annular gantry, an inner annular surface of the annular gantry forms an accommodation space, and the second imaging component is disposed in the accommodation space.

* * * * *